United States Patent
Nizzari et al.

(10) Patent No.: US 9,298,804 B2
(45) Date of Patent: *Mar. 29, 2016

(54) VARIANT DATABASE

(71) Applicant: Good Start Genetics, Inc., Cambridge, MA (US)

(72) Inventors: Marcia M. Nizzari, Needham, MA (US); Benjamin H. Breton, Woburn, MA (US); David L. Tefft, Malden, MA (US); Xavier S. Haurie, Belmont, MA (US)

(73) Assignee: Good Start Genetics, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/329,243

(22) Filed: Jul. 11, 2014

(65) Prior Publication Data

US 2014/0324869 A1    Oct. 30, 2014

Related U.S. Application Data

(63) Continuation of application No. 13/667,575, filed on Nov. 2, 2012, now Pat. No. 8,812,422.

(60) Provisional application No. 61/621,779, filed on Apr. 9, 2012.

(51) Int. Cl.
G06N 5/02     (2006.01)
G06F 17/30    (2006.01)
(Continued)

(52) U.S. Cl.
CPC .......... *G06F 17/30598* (2013.01); *G06F 19/18* (2013.01); *G06F 19/28* (2013.01); *G06N 5/02* (2013.01)

(58) Field of Classification Search
None
See application file for complete search history.

(56) References Cited

U.S. PATENT DOCUMENTS 4,683,195 A    7/1987    Mullis et al.
4,683,202 A    7/1987    Mullis
(Continued)

FOREIGN PATENT DOCUMENTS

EP    1 321 477 A1    6/2003
EP    1 564 306 A2    8/2005
(Continued)

OTHER PUBLICATIONS

Goto, S. A Study on Development of a Deductive Object-Oriented Database and Its Application to Genome Analysis. Diss. PhD Thesis, Kyushu University, 1994.*
(Continued)

*Primary Examiner* — Kakali Chaki
*Assistant Examiner* — Kevin W Figueroa
(74) *Attorney, Agent, or Firm* — Thomas C. Meyers; Brown Rudnick LLP

(57) ABSTRACT

The invention provides a system and method for describing polymorphisms or genetic variants based on information about mutations and relationships among them. The invention uses object-oriented concepts to describe variants as variant objects and relations among those variants as variant relation object, each object being an instance of an abstract class of genomic feature and able to contain any number of other objects. Information about genetic disorders is stored in association with the object that represents the pathogenic variant. Genetic test results are used to access corresponding objects to provide a report based on variants or polymorphisms in a patient's genetic material.

16 Claims, 14 Drawing Sheets

FIG. 1

(51) Int. Cl.
  *G06F 19/28* (2011.01)
  *G06F 19/18* (2011.01)

(56) References Cited

U.S. PATENT DOCUMENTS

| | | |
|---|---|---|
| 4,988,617 A | 1/1991 | Landegren et al. |
| 5,234,809 A | 8/1993 | Boom et al. |
| 5,242,794 A | 9/1993 | Whiteley et al. |
| 5,494,810 A | 2/1996 | Barany et al. |
| 5,583,024 A | 12/1996 | McElroy et al. |
| 5,604,097 A | 2/1997 | Brenner |
| 5,636,400 A | 6/1997 | Young |
| 5,674,713 A | 10/1997 | McElroy et al. |
| 5,695,934 A | 12/1997 | Brenner |
| 5,700,673 A | 12/1997 | McElroy et al. |
| 5,701,256 A | 12/1997 | Marr et al. |
| 5,830,064 A | 11/1998 | Bradish et al. |
| 5,846,719 A | 12/1998 | Brenner et al. |
| 5,863,722 A | 1/1999 | Brenner |
| 5,866,337 A | 2/1999 | Schon |
| 5,869,252 A | 2/1999 | Bouma et al. |
| 5,871,921 A | 2/1999 | Landegren et al. |
| 5,993,611 A | 11/1999 | Moroney, III et al. |
| 6,100,099 A | 8/2000 | Gordon et al. |
| 6,138,077 A | 10/2000 | Brenner |
| 6,150,516 A | 11/2000 | Brenner et al. |
| 6,172,214 B1 | 1/2001 | Brenner |
| 6,172,218 B1 | 1/2001 | Brenner |
| 6,197,508 B1 | 3/2001 | Stanley |
| 6,210,891 B1 | 4/2001 | Nyren et al. |
| 6,223,128 B1 | 4/2001 | Allex et al. |
| 6,235,472 B1 | 5/2001 | Landegren et al. |
| 6,235,475 B1 | 5/2001 | Brenner et al. |
| 6,235,501 B1 | 5/2001 | Gautsch et al. |
| 6,258,568 B1 | 7/2001 | Nyren |
| 6,274,320 B1 | 8/2001 | Rothberg et al. |
| 6,306,597 B1 | 10/2001 | Macevicz |
| 6,352,828 B1 | 3/2002 | Brenner |
| 6,360,235 B1 | 3/2002 | Tilt et al. |
| 6,361,940 B1 | 3/2002 | Van Ness et al. |
| 6,403,320 B1 | 6/2002 | Read et al. |
| 6,462,254 B1 | 10/2002 | Vernachio et al. |
| 6,489,105 B1 | 12/2002 | Matlashewski et al. |
| 6,558,928 B1 | 5/2003 | Landegren |
| 6,582,938 B1 | 6/2003 | Su et al. |
| 6,585,938 B1 | 7/2003 | Machida et al. |
| 6,613,516 B1 | 9/2003 | Christians et al. |
| 6,714,874 B1 | 3/2004 | Myers et al. |
| 6,719,449 B1 | 4/2004 | Laugharn, Jr. et al. |
| 6,818,395 B1 | 11/2004 | Quake et al. |
| 6,828,100 B1 | 12/2004 | Ronaghi |
| 6,833,246 B2 | 12/2004 | Balasubramanian |
| 6,858,412 B2 | 2/2005 | Willis et al. |
| 6,911,345 B2 | 6/2005 | Quake et al. |
| 6,913,879 B1 | 7/2005 | Schena |
| 6,948,843 B2 | 9/2005 | Laugharn, Jr. et al. |
| 7,034,143 B1 | 4/2006 | Preparata et al. |
| 7,041,481 B2 | 5/2006 | Anderson et al. |
| 7,049,077 B2 | 5/2006 | Yang |
| 7,057,026 B2 | 6/2006 | Barnes et al. |
| 7,071,324 B2 | 7/2006 | Preparata et al. |
| 7,074,564 B2 | 7/2006 | Landegren |
| 7,115,400 B1 | 10/2006 | Adessi et al. |
| 7,169,560 B2 | 1/2007 | Lapidus et al. |
| 7,211,390 B2 | 5/2007 | Rothberg et al. |
| 7,232,656 B2 | 6/2007 | Balasubramanian et al. |
| 7,244,559 B2 | 7/2007 | Rothberg et al. |
| RE39,793 E | 8/2007 | Brenner |
| 7,264,929 B2 | 9/2007 | Rothberg et al. |
| 7,282,337 B1 | 10/2007 | Harris |
| 7,297,518 B2 | 11/2007 | Quake et al. |
| 7,320,860 B2 | 1/2008 | Landegren et al. |
| 7,323,305 B2 | 1/2008 | Leamon et al. |
| 7,335,762 B2 | 2/2008 | Rothberg et al. |
| 7,351,528 B2 | 4/2008 | Landegren |
| 7,393,665 B2 | 7/2008 | Brenner |
| 7,510,829 B2 | 3/2009 | Faham et al. |
| 7,523,117 B2 | 4/2009 | Zhang et al. |
| 7,537,897 B2 | 5/2009 | Brenner et al. |
| 7,544,473 B2 | 6/2009 | Brenner |
| 7,582,431 B2 | 9/2009 | Drmanac et al. |
| 7,598,035 B2 | 10/2009 | Macevicz |
| 7,666,593 B2 | 2/2010 | Lapidus |
| 7,700,323 B2 | 4/2010 | Willis et al. |
| 7,776,616 B2 | 8/2010 | Heath et al. |
| RE41,780 E | 9/2010 | Anderson et al. |
| 7,790,388 B2 | 9/2010 | Landegren et al. |
| 7,809,509 B2 | 10/2010 | Milosavljevic |
| 7,835,871 B2 | 11/2010 | Kain et al. |
| 7,862,999 B2 | 1/2011 | Zheng et al. |
| 7,865,534 B2 | 1/2011 | Chandra et al. |
| 7,883,849 B1 | 2/2011 | Dahl |
| 7,957,913 B2 | 6/2011 | Chinitz et al. |
| 7,960,120 B2 | 6/2011 | Rigatti et al. |
| 7,985,716 B2 | 7/2011 | Yershov et al. |
| 7,993,880 B2 | 8/2011 | Willis et al. |
| 8,024,128 B2 | 9/2011 | Rabinowitz et al. |
| 8,165,821 B2 | 4/2012 | Zhang |
| 8,209,130 B1 | 6/2012 | Kennedy et al. |
| 8,283,116 B1 | 10/2012 | Bhattacharyya et al. |
| 8,462,161 B1 | 6/2013 | Barber |
| 8,463,895 B2 | 6/2013 | Arora et al. |
| 8,529,744 B2 | 9/2013 | Marziali et al. |
| 8,812,422 B2 | 8/2014 | Nizzari et al. |
| 8,847,799 B1 | 9/2014 | Kennedy et al. |
| 2001/0007742 A1 | 7/2001 | Landergren |
| 2001/0046673 A1 | 11/2001 | French et al. |
| 2002/0001800 A1 | 1/2002 | Lapidus |
| 2002/0164629 A1 | 11/2002 | Quake et al. |
| 2002/0182609 A1 | 12/2002 | Arcot |
| 2002/0187496 A1 | 12/2002 | Andersson et al. |
| 2002/0190663 A1 | 12/2002 | Rasmussen |
| 2003/0166057 A1 | 9/2003 | Hildebrand et al. |
| 2003/0177105 A1 | 9/2003 | Xiao et al. |
| 2003/0203370 A1 | 10/2003 | Yakhini et al. |
| 2003/0224384 A1 | 12/2003 | Sayood et al. |
| 2004/0106112 A1 | 6/2004 | Nilsson et al. |
| 2004/0142325 A1 | 7/2004 | Mintz et al. |
| 2004/0152108 A1 | 8/2004 | Keith et al. |
| 2004/0209299 A1 | 10/2004 | Pinter et al. |
| 2005/0026204 A1 | 2/2005 | Landegren |
| 2005/0032095 A1 | 2/2005 | Wigler et al. |
| 2005/0048505 A1 | 3/2005 | Fredrick et al. |
| 2005/0059048 A1 | 3/2005 | Gunderson et al. |
| 2005/0100900 A1 | 5/2005 | Kawashima et al. |
| 2005/0112590 A1 | 5/2005 | Boom et al. |
| 2005/0244879 A1 | 11/2005 | Schumm et al. |
| 2006/0019304 A1 | 1/2006 | Hardenbol et al. |
| 2006/0024681 A1 | 2/2006 | Smith et al. |
| 2006/0078894 A1 | 4/2006 | Winkler et al. |
| 2006/0177837 A1 | 8/2006 | Borozan et al. |
| 2006/0183132 A1 | 8/2006 | Fu et al. |
| 2006/0192047 A1 | 8/2006 | Goossen |
| 2006/0292585 A1 | 12/2006 | Nautiyal et al. |
| 2006/0292611 A1 | 12/2006 | Berka et al. |
| 2007/0020640 A1 | 1/2007 | McCloskey et al. |
| 2007/0042369 A1 | 2/2007 | Reese et al. |
| 2007/0092883 A1 | 4/2007 | Schouten et al. |
| 2007/0114362 A1 | 5/2007 | Feng et al. |
| 2007/0128624 A1 | 6/2007 | Gormley et al. |
| 2007/0161013 A1 | 7/2007 | Hantash |
| 2007/0162983 A1 | 7/2007 | Hesterkamp et al. |
| 2007/0166705 A1 | 7/2007 | Milton et al. |
| 2007/0225487 A1 | 9/2007 | Nilsson et al. |
| 2007/0244675 A1 | 10/2007 | Shai et al. |
| 2007/0264653 A1 | 11/2007 | Berlin et al. |
| 2008/0003142 A1 | 1/2008 | Link et al. |
| 2008/0014589 A1 | 1/2008 | Link et al. |
| 2008/0076118 A1 | 3/2008 | Tooke et al. |
| 2008/0081330 A1 | 4/2008 | Kahvejian |
| 2008/0269068 A1 | 10/2008 | Church et al. |
| 2008/0280955 A1 | 11/2008 | McCamish |
| 2008/0293589 A1 | 11/2008 | Shapero |
| 2009/0009904 A1 | 1/2009 | Yasuna et al. |

(56) References Cited

U.S. PATENT DOCUMENTS

| | | |
|---|---|---|
| 2009/0019156 A1 | 1/2009 | Mo et al. |
| 2009/0026082 A1 | 1/2009 | Rothberg et al. |
| 2009/0098551 A1 | 4/2009 | Landers et al. |
| 2009/0099041 A1 | 4/2009 | Church et al. |
| 2009/0105081 A1 | 4/2009 | Rodesch et al. |
| 2009/0119313 A1 | 5/2009 | Pearce |
| 2009/0127589 A1 | 5/2009 | Rothberg et al. |
| 2009/0129647 A1 | 5/2009 | Dimitrova et al. |
| 2009/0156412 A1 | 6/2009 | Boyce, IV et al. |
| 2009/0163366 A1 | 6/2009 | Nickerson et al. |
| 2009/0191565 A1 | 7/2009 | Lapidus et al. |
| 2009/0192047 A1 | 7/2009 | Parr et al. |
| 2009/0203014 A1 | 8/2009 | Wu et al. |
| 2009/0226975 A1 | 9/2009 | Sabot et al. |
| 2009/0233814 A1 | 9/2009 | Bashkirov et al. |
| 2009/0298064 A1 | 12/2009 | Batzoglou et al. |
| 2009/0318310 A1 | 12/2009 | Liu et al. |
| 2010/0035243 A1 | 2/2010 | Muller et al. |
| 2010/0035252 A1 | 2/2010 | Rothberg et al. |
| 2010/0063742 A1 | 3/2010 | Hart et al. |
| 2010/0069263 A1 | 3/2010 | Shendure et al. |
| 2010/0105107 A1 | 4/2010 | Hildebrand et al. |
| 2010/0137143 A1 | 6/2010 | Rothberg et al. |
| 2010/0137163 A1 | 6/2010 | Link et al. |
| 2010/0159440 A1* | 6/2010 | Messier et al. ............ 435/5 |
| 2010/0188073 A1 | 7/2010 | Rothberg et al. |
| 2010/0197507 A1 | 8/2010 | Rothberg et al. |
| 2010/0216151 A1 | 8/2010 | Lapidus et al. |
| 2010/0248984 A1 | 9/2010 | Shaffer et al. |
| 2010/0282617 A1 | 11/2010 | Rothberg et al. |
| 2010/0285578 A1 | 11/2010 | Selden et al. |
| 2010/0297626 A1 | 11/2010 | McKernan et al. |
| 2010/0300559 A1 | 12/2010 | Schultz et al. |
| 2010/0300895 A1 | 12/2010 | Nobile et al. |
| 2010/0301042 A1 | 12/2010 | Kahlert |
| 2010/0301398 A1 | 12/2010 | Rothberg et al. |
| 2010/0304982 A1 | 12/2010 | Hinz et al. |
| 2010/0330619 A1 | 12/2010 | Willis et al. |
| 2011/0004413 A1 | 1/2011 | Carnevali et al. |
| 2011/0009278 A1 | 1/2011 | Kain et al. |
| 2011/0015863 A1 | 1/2011 | Pevzner et al. |
| 2011/0021366 A1 | 1/2011 | Chinitz et al. |
| 2011/0034342 A1* | 2/2011 | Fox ............................ 506/7 |
| 2011/0098193 A1 | 4/2011 | Kingsmore et al. |
| 2011/0159499 A1 | 6/2011 | Hindson et al. |
| 2011/0166029 A1 | 7/2011 | Margulies et al. |
| 2011/0230365 A1 | 9/2011 | Rohlfs et al. |
| 2011/0257889 A1 | 10/2011 | Klammer et al. |
| 2011/0301042 A1 | 12/2011 | Steinmann et al. |
| 2012/0015050 A1 | 1/2012 | Abkevich et al. |
| 2012/0021930 A1 | 1/2012 | Schoen et al. |
| 2012/0059594 A1 | 3/2012 | Hatchwell et al. |
| 2012/0115736 A1 | 5/2012 | Bjornson et al. |
| 2012/0164630 A1 | 6/2012 | Porreca et al. |
| 2012/0165202 A1 | 6/2012 | Porreca et al. |
| 2012/0179384 A1 | 7/2012 | Kuramitsu et al. |
| 2012/0214678 A1 | 8/2012 | Rava et al. |
| 2012/0252020 A1 | 10/2012 | Shuber |
| 2012/0252684 A1 | 10/2012 | Selifonov et al. |
| 2013/0222388 A1 | 8/2013 | McDonald |
| 2013/0268474 A1 | 10/2013 | Nizzari et al. |
| 2013/0275103 A1 | 10/2013 | Struble et al. |
| 2013/0344096 A1 | 12/2013 | Chiang et al. |
| 2014/0129201 A1 | 5/2014 | Kennedy et al. |

FOREIGN PATENT DOCUMENTS

| | | | |
|---|---|---|---|
| EP | 2 437 191 A2 | 4/2012 | |
| WO | 95/11995 A1 | 5/1995 | |
| WO | 96/19586 A1 | 6/1996 | |
| WO | 98/14275 A1 | 4/1998 | |
| WO | 98/44151 A1 | 10/1998 | |
| WO | 00/18957 A1 | 4/2000 | |
| WO | 02/25570 A2 | 3/2002 | |
| WO | 02/093453 A2 | 11/2002 | |
| WO | 2004/018497 | 3/2004 | |
| WO | 2004/031765 A1 | 4/2004 | |
| WO | 2004/083819 A2 | 9/2004 | |
| WO | 2005/003304 A2 | 1/2005 | |
| WO | 2005/031200 A1 | 4/2005 | |
| WO | 2007/010251 A2 | 1/2007 | |
| WO | 2007/107717 A1 | 9/2007 | |
| WO | 2007/123744 | 11/2007 | |
| WO | 2007/135368 A2 | 11/2007 | |
| WO | 2009/036525 A2 | 3/2009 | |
| WO | 2010/024894 A1 | 3/2010 | |
| WO | 2010/126614 A2 | 11/2010 | |
| WO | 2011/006020 A1 | 1/2011 | |
| WO | 2012/040387 A1 | 3/2012 | |
| WO | 2012/051208 A2 | 4/2012 | |
| WO | 2012/087736 A1 | 6/2012 | |
| WO | 2012/109500 A2 | 8/2012 | |
| WO | 2012/134884 A1 | 10/2012 | |
| WO | 2012/170725 A2 | 12/2012 | |
| WO | 2013/058907 A1 | 4/2013 | |
| WO | 2013/191775 A2 | 12/2013 | |

OTHER PUBLICATIONS

Alm, Elizabeth Wheeler, et al. "The oligonucleotide probe database." Applied and Environmental Microbiology 62.10 (1996): 3557.*

Ng et al., 2009, Targeted capture and massively parallel sequencing of 12 human exomes, Nature 461(7261):272-6.

Nicholas, et al., 2002, Strategies for multiple sequence alignment, Biotechniques 32:572-91.

Nickerson et al., 1990, Automated DNA diagnostics using an ELISA-based oligonucleotide ligation assay, Proc. National Academy of Science 87:8923-7.

Nielsen et al., 1999, Peptide Nucleic Acids, Protocols and Applications (Norfolk: Horizon Scientific Press, 1-19).

Nilsson et al., 2006, Analyzing genes using closing and replicating circles, Trends in Biotechnology 24:83-8.

Ning et al., 2001, SSAHA: A fast search method for large DNA databases, Genome Research 11(10): 1725-9 (2001).

Non-final Office Action mailed Mar. 12, 2014, for U.S. Appl. No. 14/132,364, filed Dec. 18, 2013 (8 pages).

Nordhoff et al., 1993, Ion stability of nucleic acids in infrared matrix-assisted laser desorption/ ionization mass spectrometry, Nucl Acid Res 21(15):3347-57.

Nuttle et al., 2013, Rapid and accurate large-scale genotyping of duplicated genes and discovery of interlocus gene conversions, Nat Methods 10(9): 903-909, and Supplementary Information (58 pages).

Nuttle et al., 2014, Resolving genomic disorder-associated breakpoints within segmental DNA duplications using massively parallel sequencing, Nature Protocols 9(6):1496-1513.

Oefner et al., 1996, Efficient random sub-cloning of DNA sheared in a recirculating point-sink flow system, Nucleic Acids Res 24(20):3879-3886.

Oka et al., 2006, Detection of loss of heterozygosity in the p53 gene in renal cell carcinoma and bladder cancer using the polymerase chain reaction, Molecular Carcinogenesis 4(1):10-13.

Okoniewski et al., 2013, Precise breakpoint localization of large genomic deletions using PacBio and Illumina next-generation sequencers, Biotechniques 54(2):98-100.

Oliphant, et al., 2002, BeadArray?Technology: Enabling an Accurate, Cost-Effective Approach to High-Throughput Genotyping, Biotechniques Suppl:56-8, 60-1.

Ordahl et al., 1976, Sheared DNA fragment sizing: comparison of techniques, Nucleic Acids Res 3:2985-2999.

Ostrer et al., 2001, A genetic profile of contemporary Jewish populations, Nature Reviews Cancer 2:891-8.

Owens et al., 1998, Aspects of oligonucleotide and peptide sequencing with MALDI and electrospray mass spectrometry, Bioorg Med Chem 6:1547-1554.

Parameswaran et al., 2007, A pyrosequencing-tailored nucleotide barcode design unveils opportunities for large-scale sample multiplexing, Nucleic Acids Research 35:e130, pp. 1-9.

(56) References Cited

OTHER PUBLICATIONS

Parameswaran et al., 2007, A pyrosequencing-tailored nucleotide barcode design unveils opportunities for large-scale sample multiplexing, Nucleic Acids Research 35:e130, Supplementary Material, 18 pages.
Patent Examination Report No. 1 for Patent Application No. 2010242073, dated Aug. 12, 2014.
Pearson et al., 1988, Improved tools for biological sequence comparison, PNAS 85(8):2444-8.
Pertea et al., 2003, TIGR gene indices clustering tools (TGICL), Bioinformatics 19(5):651-52.
Pieles et al., 1993, Matrix-assisted laser desorption ionization time-of-flight mass spectrometry: A powerful tool for the mass and sequence analysis of natural and modified oligonucleotides, Nucleic Acids Res 21:3191-3196.
Pinho, 2013, MFCompress: a compression tool for FASTA and multi-FASTA data, Bioinformatics 30(1):117-8.
Porreca et al., 2007, Multiplex amplification of large sets of human exons, Nature Methods 4:931-6.
Porreca et al., 2013, Analytical performance of a Next-Generation DNA sequencing-based clinical workflow for genetic carrier screening, American Society of Human Genetics 63rd Annual Meeting, Abstract, Oct. 22, 2013 (2 pages).
Procter et al., 2006, Molecular Diagnosis of Prader-Willi and Angelman Syndromes by Methylation-Specific Melting Analysis and Methylation-Specific Multiplex Ligation-Dependent Probe Amplification, Clinical Chemistry 52(7):1276-83.
Quail et al., 2010, DNA: Mechanical Breakage, Encyclopedia of Life Sciences 2010.
Rambaut et al., 1997, Seq-Gen:an application for the Monte Carlo simulation of DNA sequence evolution along phylogenetic trees, Bioinformatics (formerly CABIOS) 13:235-38.
Richards, 2008, ACMG recommendations for standards for interpretation and reporting of sequence variations: Revisions 2007, Genet Med 10:294-300.
Richter et al., 2008, MetaSim—A Sequencing Simulator for Genomics and Metagenomics, PLOS ONE 3:e3373.
Roberts, 1980, Restriction and modification enzymes and their recognition sequences, Nucleic Acids Res 8(1):r63-r80.
Rodriguez, 2010, Constructions from Dots and Lines, Bull Am Soc Inf Sci Tech 36(6):35-41, available at http://arxiv.org/pdf/1006.2361.pdf.
Rosendahl et al., 2013, CFTR, SPINK1, CTRC and PRSS1 variants in chronic pancreatitis: is the role of mutated CFTR overestimated?, Gut 62:582-592.
Rothberg et al., 2011, An integrated semiconductor device enabling non-optical genome sequencing, Nature 475:348-352.
Rowntree and Harris, 2003, The phenotypic consequences of CFTR mutations, Ann Hum Gen 67:471-485.
S. Gustincich et al., BioTechniques, 1991, 11: 298-302.
Sanger et al., 1977, DNA Sequencing with chain-terminating inhibitors, PNAS 74(12):5463-5467.
Santa Lucia, John Jr., 1998, A unified view of polymer, dumbbell, and oligonucleotide DNA nearest-neighbor thermodynamics, Proc. National Academy of Science USA 95:1460-5.
Sargent, T.D., 1988, Isolation of Differentially Expressed Genes, Methods in Enzymology 152:432.
Sauro, 2004, How Do You Calculate a Z-Score/ Sigma Level?, https://www.measuringusability.com/zcalc.htm (online publication).
Sauro, 2004, What's a Z-Score and Why Use it in Usability Testing?, https://www.measuringusability.com/z.htm (online publication).
Schadt et al., 2010, A window into third-generation sequencing, Human Molecular Genetics 19(R2):R227-40.
Schatz et al., 2010, Assembly of large genomes using second-generation sequencing, Genome Res., 20:1165-1173.
Schiffman, 2009, Molecular inversion probes reveal patterns of 9p21 deletion and copy number aberrations in childhood leukemia, Cancer Genetics and Cytogenetics 193:9-18.
Schrijver, 2005, Diagnostic testing by CFTR gene mutation analysis in a large group of Hispanics, J Mol Diag 7(2):289-299.
Schuette et al., 1995, Sequence analysis of phosphorothioate oligonucleotides via matrix-assisted laser desorption ionization time-of-flight mass spectrometry, J. Pharm. Biomed. Anal 13:1195-1203.
Schwartz et al., 2009, Identification of Cystic Fibrosis Variants by Polymerase Chain Reaction/Oligonucleotide Ligation Assay, The Journal of Molecular Diagnostics 11(3):211-15.
Schwartz, Stuart, 2011, Clinical Utility of Single Nucleotide Polymorphism Arrays, Clinics in Laboratory Medicine 31(4):581-94.
Sequeira et al., 1997, Implementing generic, object-oriented models in biology, Ecological Modeling 94.1:17-31.
Pastor et al., 2010, Conceptual Modeling of Human Genome Mutations: A Dichotomy Between What we Have and What we Should Have, 2010 Proceedings BIOSTEC Bioinformatics, pp. 160-166. ISBN: 978-989-674-019-1.
Paton et al., 2000, Conceptual modelling of genomic information, Bioinformatics 16(6):548-57.
Supplementary European Search Report mailed Oct. 26, 2015, for European patent application 13776268.8, being a regional stage entry of International Application No. PCT/US2013/032885 with International Filing Date Mar. 19, 2013 (7 pages.
Sievers et al., 2011, Fast, scalable generation of high-quality protein multiple sequence alignments using Clustal Omega, Mol Syst Biol 7:539.
Simpson et al., 2009, ABySS: A parallel assembler for short read sequence data, Genome Research 19(6):1117-23.
Slater, G., & Birney, E, 2005, Automated generation of heuristics for biological sequence comparison, BMC Bioinformatics 6:31.
Smirnov et al., 1996, Sequencing oligonucleotides by exonuclease digestion and delayed extraction matrix-assisted laser desorption ionization time-of-flight mass spectrometry, Anal Biochem 238:19-25.
Soni and Meller, 2007, Progress toward ultrafast DNA sequencing using solid-state nanopores, Clin Chem 53:1996-2001.
Soni, G. V., & Meller, A, 2007, Progress toward ultrafast DNA sequencing using solid-state nanopores, Clin Chem 53: 1996-2001.
Spanu et al., 2010, Genome expansion and gene loss in powdery mildew fungi reveal tradeoffs in extreme parasitism, Science 330(6010): 1543-46.
Strom, 2005, Mutation detection, interpretation, and applications in the clinical laboratory setting, Mutat Res 573:160-67.
Summerer, Daniel, 2009, Enabling technologies of genomic-scale sequence enrichment for targeted high-throughput sequencing, Genomics 94:363-8.
Sunnucks et al., 1996, Microsatellite and chromosome evolution of parthenogenetic sitobion aphids in Australia, Genetics 144:747-756.
Supplementary European Search Report for EP Application No. 10770071.8 dated Nov. 8, 2012, 17 pages.
Supplementary European Search Report issued Aug. 26, 2014, for European Patent Application No. 12765217.0, filed Mar. 20, 2012, 5 pages.
Thauvin-Robinet et al., 2009, The very low penetrance of cystic fibrosis for the R117H mutation: a reappraisal for genetic counseling and newborn screening, J Med Genet 46:752-758.
Thiyagarajan et al., 2006, PathogenMIPer: a tool for the design of molecular inversion probes to detect multiple pathogens, BMC Bioinformatics 7:500.
Thompson et al., 1994, Clustal W: improving the sensitivity of progressive mulitple sequence alignment through sequence weighting, position-specific gap penalties and weight matrix choice, Nuc Acids Res 22:4673-80.
Thompson et al., 1994, Clustal W: improving the sensitivity of progressive multiple sequence alignment through sequence weighting, position-specific gap penalities and matrix choice, Nucl. Acids. Res., 22:4673-80.
Thompson et al., 2011, The properties and applications of single-molecule DNA sequencing, Genome Biology 12(2):217, 10 pages.
Thorstenson et al., 1998, An Automated Hydrodynamic Process for Controlled, Unbiased DNA Shearing, Genome Methods 8:848-55.
Thorvaldsdottir et al., 2012, Integrative GenomicsViewer (IGV): high-performance genomics data visualization and exploration, Briefings in Bioinformatics 24(2):178-92.

(56) References Cited

OTHER PUBLICATIONS

Tokino, 1996, Characterization of the human p57 KIP2 gene: alternative splicing, insertion/deletion polymorphisms in VNTR sequences in the coding region, and mutational analysis, Human Genetics 96:625-31.
Turner et al., 2009, Massively parallel exon capture and library-free resequencing across 16 genomes, Nature Methods 6:315-316, and Supplementary Materials (14 pages).
Turner et al., 2009, Methods for Genomic Partitioning, Annual Review of Genomics and Human Genetics 10:263-84.
Umbarger et al., 2013, Detecting contamination in Next Generation DNA sequencing libraries, American Society of Human Genetics 63rd Annual Meeting, Abstract, Oct. 22, 2013 (2 pages).
Umbarger, 2014, Next-generation carrier screening, Genet Med 16:132-40.
Veeneman, 2012, Oculus: faster sequence alignment by streaming read compression, BMC Bioinformatics 13:297.
Wallace & Miyada, 1987, Oligonucleotide probes for the screening of recombinant DNA libraries, Methods Enzymol 152:432-442.
Wallace et al., 1979, Hybridization of synthetic oligodeoxyribonucteotides to dp x 174DNA:the effect of single base pair mismatch, Nucleic Acids Research 6:3543-3557.
Wang et al., 2005, Allele quantification using molecular inversion probes (MIP), Nucleic Acids Research 33(21):e183.
Warner et al., 1996, A general method for the detection of large CAG repeat expansions by fluorescent PCR, Journal Medical Genetics 33(12):1022-6.
Warren et al., 2007, Assembling millions of short DNA seuqences using SSAKE, Bioinformatics 23(4):500-501.
Watson et al., 2004, Cystic fibrosis population carrier screening: 2004 revision of American College of Medical Genetics mutation panel, Genetics in Medicine 6(5):387-391.
Williams , 2003, Restriction Endonucleases Classification, Properties, and Applications, Molecular Biotechnology 23(3):225-43.
Wittung et al., 1997, Extended DNA-Recognition Repertoire of Peptide Nucleic Acid (PNA): PNA-dsDNA Triplex Formed with Cytosine-Rich Homopyrimidine PNA, Biochemistry 36:7973.
Wu & Aboleneen, 2001, Improved oligonucleotide sequencing by alkaline phosphatase and exonuclease digestions with mass spectrometry, Anal Biochem 290:347-352.
Wu et al., 1998, Sequencing regular and labeled oligonucleotides using enzymatic digestion and ionspray mass spectrometry, Anal Biochem 263:129-138.
Yau et al., 1996, Accurate diagnosis of carriers of deletions and duplications in Duchenne/Becker muscular dystrophy by fluorescent dosage analysis, Journal Medical Genetics 33(7):550-8.
Ye et al., 2009, Pindel: a pattern growth approach to detect break points of large deletions and medium sized insertions from paired-end short reads, Bioinformatics 25(21):2865-71.
Yoo et al., 2009, Applications of DNA Microarray in Disease Diagnostics, Journal of Microbiology and Biotechnology 19(7):635-46.
Yoshida et al., 2004, Role of BRCA1 and BRCA2 as regulators of DNA repair, transcription, and cell cycle in response to DNA damage, Cancer Science 95(11)866-71.
Yu, 2007, A novel set of DNA methylation markers in urine sediments for sensitive/specific detection of bladder cancer, Clin Cancer Res 13(24):7296-7304.
Yuan, 1981, Structure and mechanism of multifunctional restriction endonucleases, Ann Rev Biochem 50:285-319.
Zerbino and Birney, Velvet: Algorithms for de novo short read assembly using de Bruijn graphs, Genome Research 18(5):821-829.
Zhang et al., 2011, Is Mitochondrial tRNAphe Variant m.593T.Ca Synergistically Pathogenic Mutation in Chinese LHON Families with m.11778G.A? PLOS ONE 6(10):e26511.
Zhao et al., 2009, PGA4genomics for comparative genome assembly based on genetic algorithm optimization, Genomics. 94(4):284-6.
Zheng et al., 2011, iAssembler: a package for de novo assembly of Roche-454/Sanger transcriptome sequences, BMC Bioinformatics 12:453.
Zhou, 2014, Bias from removing read duplication in ultra-deep sequencing experiments, Bioinformatics 30(8):1073-1080.
Zimmerman et al., 2010, A novel custom resequencing array for dilated cardiomyopathy, Genetics in Medicine 12(5):268-78.
Dudley et al., 2009, A Quick Guide for Developing Effective Bioinformatics Programming Skills, PLOS Comput Biol 5(12):e1000589.
Examination Report from the European Patent Office for EP 10770071.8 dated Jul. 16, 2013, 5 pages.
Extended European Search Report for Application No. 12765217.0 dated Aug. 26, 2014, (5 pages).
Fares et al., 2008, Carrier frequency of autosomal-recessive disorders in the Ashkenazi Jewish population: should the rationale for mutation choice for screening be reevaluated?, Prenatal Diagnosis 28:236-41.
Faulstich et al., 1997, A sequencing method for RNA oligonucleotides based on mass spectrometry, Anal Chem 69:4349-4353.
Faust, 2014, SAMBLASTER: fast duplicate marking and structural variant read extraction, Bioinformatics published online May 7, 2014.
Fitch, 1970, Distinguishing homologs from analogous proteins, Syst Biol 19(2):99-113.
Frey, 2006, Statistics Hacks 108-115.
Friedenson, 2005, BRCA1 and BRCA2 Pathways and the Risk of Cancers Other Than Breast or Ovarian, Medscape General Medicine 7(2):60.
Furtado et al., 2011, Characterization of large genomic deletions in the FBN1 gene using multiplex ligation-dependent probe amplification, BMC Medical Genetics 12:119 (7 pages).
Garber, 2008, Fixing the front end, Nature Biotechnology 26(10):1101-04.
Gemayel et al., 2010, Variable Tandem Repeats Accelerate Evolution of Coding and Regulatory Sequences, Annual Review of Genetics 44:445-77.
Glover et al., 1995, Sequencing of oligonucleotides using high performance liquid chromatography and electrospray mass spectrometry, Rapid Conn Mass Spec 9:897-901.
Gnirke et al., 2009, Solution hybrid selection with ultra-long oligonucleotides for massively parallel targeted sequencing, nature biotechnology 27:182-9.
Goto et al., 2010, BioRuby: bioinformatics software for the Ruby programming language, Bioinformatics 26(20):2617-9.
Guerrero-Fernandez, 2013, FQbin: a compatible and optimize dformat for storing and managing sequence data, IWBBIO Proceedings, Granada 337-344.
Gut & Beck, 1995, A procedure for selective DNA alkylation and detection by mass spectrometry, Nucl Acids Res 23(8):1367-1373.
Hallam, 2014, Validation for clinical use of, and initial clinical experience with, a novel approach to population-based carrier screening using high-throughput, next-generation DNA sequencing, J Mol Diagn 16:180-89.
Hammond et al., 1996, Extraction of DNA from preserved animal specimens for use in randomly amplified polymorphic DNA analysis, An Biochem 240:298-300.
Hardenbol et al., 2003, Multiplexed genotyping with sequence-tagged molecular inversion probes, nature biotechnology 21:673-8.
Hardenbol et al., 2005, Highly multiplexed molecular inversion probe genotyping: over 10,000 targeted SNPs genotyped in a single tube assay, Genome Res 15:269-75.
Harris et al., 2006, Defects Can Increase the Melting Temperature of DNA-Nanoparticle Assemblies, The Journal of Physical Chemistry B 110:16393-6.
Harris et al., 2008, Single-Molecule DNA Sequencing of a Viral Genome, Science 320:106-9.
Hiatt et al., 2013, Single molecule molecular inversion probes for targeted, high-accuracy detection of low-frequency variation, Genome Research 23:843-54.
Hodges et al., 2007, Genome-wide in situ exon capture for selective resequencing, nature genetics 29:1522-7.
Holland et al., 2008, BioJava: an open-source framework for bioinformatics, Bioinformatics 24(18):2096-97.
Homer, 2009, BFAST: An alignment tool for large scale genome resequencing, PLoS ONE 4(11):e7767.

(56) References Cited

OTHER PUBLICATIONS

Huang et al., 2008, Comparative analysis of common CFTRpolymorphisms poly-T, TGrepeats and M470V in a healthy Chinese population, World J Gastroenterol 14(12):1925-30.
Husemann, P. & Stoye, 2009, Phylogenetic Comparative Assembly, Algorithms in Bioinformatics: 9th International Workshop, pp. 145-156, Salzberg, S., and Warnow, T., Eds. Springer-Verlag, Berlin Heidelberg.
International Preliminary Report on Patentability for PCT/US2010/01293, dated Oct. 28, 2010.
International Search Report and Written Opinion for international application No. PCT/US13/62842 with international filed Oct. 1, 2013, ISR/WO mailed Feb. 4, 2014 (10 pages).
International Search Report and Written Opinion for PCT/US13/61691 mailed Jan. 10, 2014 (10 pages).
International Search Report and Written Opinion mailed Apr. 3, 2012, for International Patent Application No. PCT/US2011/065098, filed Dec. 15, 2011 (8 pages).
International Search Report and Written Opinion mailed Aug. 12, 2013, for International Patent Application No. PCT/US13/36575, filed Apr. 15, 2013 (9 pages).
International Search Report and Written Opinion mailed Dec. 9, 2014, for International Patent Application No. PCT/US14/28212, filed Mar. 14, 2014 (11 pages).
International Search Report and Written Opinion mailed Feb. 25, 2013 for International Patent Application No. PCT/US12/55362.
International Search Report and Written Opinion mailed Jan. 7, 2015, for International Patent Application No. PCT/US14/60256, filed Oct. 13, 2014 (12 pages).
International Search Report and Written Opinion mailed Jun. 10, 2013, for International Patent Application No. PCT/US13/33435, filed Mar. 22, 2013 (6 pages).
International Search Report and Written Opinion mailed Jun. 14, 2012, for International Patent Application No. PCT/US12/29790, filed Mar. 20, 2012 (8 pages).
International Search Report and Written Opinion mailed Nov. 1, 2013, for International Patent Application No. PCT/US2013/044039, filed Jun. 4, 2013 (6 pages).
International Search Report and Written Opinion mailed on Feb. 4, 2014, for Patent Application No. PCT/US13/62842, filed Oct. 1, 2013 (5 pages).
International Search Report and Written Opinion mailed on Jan. 29, 2015, for Patent Application No. PCT/US14/61138, filed Oct. 17, 2014, (11 pages).
International Search Report and Written Opinion mailed on Jan. 29, 2015, for Patent Application No. PCT/US2014/060056, filed Oct. 10, 2014, (14 pages).
International Search Report and Written Opinion mailed on Jun. 28, 2013, for Patent Application No. PCT/US2013/032885, filed Mar. 19, 2013 (9 pages).
International Search Report and Written Opinion mailed on Oct. 28, 2010, for Patent Application No. PCT/US2010/001293, filed Apr. 30, 2010 (8 pages).
International Search Report and Written Opinion mailed on Sep. 3, 2014 for International Patent Application No. PCT/US14/27324, filed Mar. 14, 2014 (8 pages).
Iqbal et al., 2012, De novo assembly and genotyping of variants using colored de Bruijn graphs, Nature Genetics, 44(2):226-233.
Jaijo et al., 2010, Microarray-Based Mutation Analysis of 183 Spanish Families with Usher Syndrome, Investigative Ophthalmology & Visual Science 51(3):1311-7.
Jensen, 2001, Orthologs and paralogs—we need to get it right, Genome Biol 2(8):1002-1002.3.
Jones et al., 2008, Core Signaling Pathways in Human Pancreatic Cancers Revealed by Global Genomic Analyses, Science 321(5897):1801-1806.
Ageno et al., 1969, The alkaline denaturation of DNA, Biophys J 9:1281-1311.

Akhras M.S., et al., 2007, Connector Inversion Probe Technology: A Powerful OnePrimer Multiplex DNA Amplification System for Numerous Scientific Applications PLOS ONE 2(9):e915.
Alazard et al., 2002, Sequencing of production-scale synthetic oligonucleotides by enriching for coupling failures using matrix-assisted laser desorption/ ionization time-of-flight mass spectrometry, Analytical biochemistry 301:57-64.
Alazard et al., 2005, Sequencing Oligonucleotides by Enrichment of Coupling Failures Using Matrix-Assisted Laser Desorption/Ionization Time-of-Flight Mass Spectrometry, Current Protocols in Nucleic Acid Chemistry 10.10.1-10.10.7.
Albert, 2007, Direct selection of human genomic loci by microarray hybridization, Nature Methods 4(11):903-5.
Aljanabi and Martinez, 1997, Universal and rapid salt-extraction of high quality genomic DNA for PCR-based techniques, Nucl. Acids Res 25:4692-4693.
Antonarakis and the Nomenclature Working Group, 1998, Recommendations for a nomenclature system for human gene mutations, Human Mutation 11:1-3.
Australian Patent Examination Report No. 1 issued Aug. 12, 2014, for Australian Patent Application No. 2010242073, filed Apr. 30, 2010, (4 pages).
Ball et al., 2009, Targeted and genome-scale strategies reveal gene-body methylation signatures in human cells, Nature Biotechnology, 27:361-8.
Balzer et al., 2013, Filtering duplicate reads from 454 pyrosequencing data, Bioinformatics 29(7):830-836.
Barany, 1991, Genetic disease detection and DNA amplification using cloned thermostable ligase, PNAS, 88:189-193.
Barany, 1991, The Ligase Chain Reaction in a PCR World, Genome Research, 1:5-16.
Bau et al., 2008, Targeted next-generation sequencing by specific capture of multiple genomic loci using low-volume microfluidic DNA arrays, Analytical and bioanalytical chem 393(1):171-5.
Beer and Moudrianakis, 1962, Determination of base sequence in nucleic acids with the electron microscope: visibility of a marker, PNAS 48(3):409-416.
Bell et al., 2011, Carrier testing for severe childhood recessive diseases by next-generation sequencing, Science Translational Medicine 3(65ra4), 15 pages.
Benner et al., 2001, Evolution, language and analogy in functional genomics, Trends in Genetics 17:414-8.
Bentzley et al., 1996, Oligonucleotide sequence and composition determined by matrix-assisted laser desorption/ionization, Anal Chem 68:2141-2146.
Bentzley et al., 1998, Base specificity of oligonucleotide digestion by calf spleen phosphodiesterase with matrix-assisted laser desorption ionization analysis, Anal Biochem 258:31-37.
Bickle et al., 1993, Biology of DNA Restriction, Microbiological Reviews 57(2):434-50.
Bonfield et al., 2013, Compression of FASTQ and SAM format sequencing data, PLoS One 8(3):e59190.
Bose et al., 2012, BIND—An algorithm for loss-less compression of nucleotide sequence data, J Biosci 37(4):785-789.
Boyden, 2013, High-throughput screening for SMN1 copy numbers loss by next-generation sequencing, American Society of Human Genetics 63rd Annual Meeting, Abstract, Oct. 22, 2013 (2 pages).
Boyer, 1971, DNA restriction and modification mechanisms in bacteria, Ann Rev Microbiol 25:153-76.
Braasch et al., 2001, Locked nucleic acid (LNA): ¢ ne-tuning the recognition of DNA and RNA, Chemistry & Biology 8(1):1-7.
Braslaysky et al., 2003, Sequence information can be obtained from single DNA molecules, Proceedings of the National Academy of Sciences, (USA) 100:3960-4.
Brown et al., 1979, Chemical synthesis and cloning of a tyrosine tRNA gene, Methods Enzymol., 68:109.
Browne 2002, Metal ion-catalyzed nucleic Acid alkylation and fragmentation, J Am Chem Soc 124(27):7950-7962.
Brownstein, 2014, An international effort towards developing standards for best practices in analysis, interpretation and reporting of clinical genome sequencing results in the CLARITY Challenge, Genome Biol 15:R53.

(56) References Cited

OTHER PUBLICATIONS

Bunyan et al., 2004, Dosage analysis of cancer predisposition genes by multiplex ligation-dependent probe amplification, British Journal of Cancer, 91(6):1155-59.
Burrow & Wheeler, 1994, A block-sorting lossless data compression algorithm, Technical Report 124, Digital Equipment Corporation, CA.
Castellani, 2008, Consenses on the use of and interpretation of cystic fibrosis mutation analysis in clinical practice, J Cyst Fib 7:179-196.
Challis et al., 2012, An integrative variant analysis suite for whole exome next-generation sequencing data, BMC Informatics 13(8):1-12.
Chan et al., 2011, Natural and engineered nicking endonucleases—from cleavage mechanism to engineering of strand-specificity, Nucl Acids Res 39(1):1-18.
Chennagiri, 2013, A generalized scalable database model for storing and exploring genetic variations detected using sequencing data, American Society of Human Genetics 63rd Annual Meeting, Abstract, Oct. 22, 2013 (2 pages).
Chevreux et al., 1999, Genome Sequence Assembly Using Trace Signals and Additional Sequence Information, Computer Science and Biology: Proceedings of the German Conference on Bioinformatics (GCB) 99:45-56.
Chirgwin et al., 1979, Isolation of biologically active ribonucleic acid from sources enriched in ribonuclease, Biochemistry, 18:5294-99.
Choe et al., 2010, Novel CFTR Mutations in a Korean Infant with Cystic Fibrosis and Pancreatic Insufficiency, J Korean Med Sci 25:163-5.
Ciotti et al., 2004, Triplet Repeat Primed PCR (TP PCR) in Molecular Diagnostic Testing for Friedrich Ataxia, Journal of Molecular Diagnostics 6(4):285-9.
Cock et al., 2009, The Sanger FASTQ file format for sequences with quality scores, and the Solexa/Illumina FASTQ variants, Nucleic Acids Res 38(6):1767-1771.
Collins et al., 2004, Finishing the euchromatic sequence of the human genome, Nature 431.7011:931-45.
Dahl et al., 2005, Multiplex amplification enabled by selective circularization of large sets of genomic DNA fragments, Nucleic Acids Research 33:e71.
Danecek, 2011, The variant call format and VCFtools, Bioinformatics 27(15):2156-58.
de la Bastide, M. & McCombie, 2007, W. R., Assembling genome DNA sequences with PHRAP, Current Protocols in Bioinformatics, 17:11.4.1-11.4.15.
Delcher et al., 1999, Alignment of whole genomes, Nucleic Acids Research, 27:11.
Deng et al., 2009, Targeted bisulfite sequencing reveals changes in DNA methylation associated with nuclear reprogramming, nature biotechnology 27:353-60 (and supplement).
Deng et. al., 2012, Supplementary Material, Nature Biotechnology, S1-1-S1-1 1, Retrieved from the Internet: URL: http://www.nature.com/nbt/journal/v27/n4/extref/nbt.1530-S1.pdf, retrieved on Oct. 24, 2012.
Deng J., et al., Nature Biotechnology: doi:10.1038/nbt.1530, Supplement, 11 pages.
DiGuistini et al., 2009, De novo sequence assembly of a filamentous fungus uisng Sanger, 454 and Illumina seqeunce data, Genome Biology, 10:R94.
Dong and Yu, 2011, Mutation Surveyor: an in silico tool for sequencing analysis, Methods Mol Biol 760:223-37.
Dore et al., 1969, The Alkaline Denaturation of DNA, Biophysical Journal 9(11):1281-1311.
Kennedy et al., 2013, Accessing more human genetic variation with short sequencing reads, American Society of Human Genetics 63rd Annual Meeting, Abstract, Oct. 22, 2013 (2 pages).
Kent, W.J., 2002, BLAT—The BLAST-like alignment tool, Genome Research 4: 656-664.
Kircher et al., 2010, High-througput DNA sequencing—concepts and limitations, Bioassays 32:524-36.
Kirpekar et al., 1994, Matrix assisted laser desorption/ionization mass spectrometry of enzymatically synthesized RNA up to 150 kDa, Nucleic Acids Res 22:3866-3870.
Klein et al., 2011,LOCAS—A low coverage sequence assembly tool for re-sequencing projects, PLoS One 6(8) article 23455.
Kneen, 1998, Green fluorescent protein as a noninvasive intracellular pH indicator, Biophys J 74(3):1591-99.
Koboldt et al., 2009, VarScan: variant detection in massively parallel sequencing of individual and pooled samples, Bioinformatics 25:2283-85.
Krawitz, 2010, Microindel detection in short-read sequence data, Bioinformatics 26(6):722-729.
Kreindler, 2010, Cystic fibrosis: exploiting its genetic basis in the hunt for new therapies, Pharmacol Ther 125(2)219-229.
Krishnakumar et al., 2008, A comprehensive assay for targeted multiplex amplification of human DNA sequences, PNAS 105:9296-301.
Kumar and Blaxter, 2010, Comparing de novo assemblers for 454 transcriptome data, BMC Genomics 11:571.
Kurtz et al., 2004, Versatile and open software for comparing large genomes, Genome Biology, 5:R12.
Lam et al., 2008, Compressed indexing and local alignment of DNA, Bioinformatics 24(6):791-97.
Langmead et al., 2009, Ultrafast and memory-efficient alignment of short DNA sequences to the human genome, Genome Biology, 10:R25.
Larkin et al., 2007, Clustal W and Clustal X version 2.0, Bioinformatics, 23(21):2947-2948.
Lecompte et al., 2001, Multiple alignment of complete sequences (MACS) in the post-genomic era, Gene 270:17-30.
Li & Durbin, 2009, Fast and accurate short read alignment with Burrows-Wheeler transform, Bioinformatics, 25 (14)1754-60.
Li & Durbin, 2010, Fast and accurate long-read alignment with Burrows-Wheeler transform, Bioinformatics 26 (5):589-95.
Li and Durbin, 2009, Fast and accurate long-read alignment with Burrows-Wheeler Transform, Bioinformatics, 25:1754-60 (2009).
Li and Stoneking, 2012, A new approach to detecting low-level mutations in next-generation sequence data, Genome Biol 13:1-15.
Li et al., 2008, SOAP: short oligonucleotide alignment program, Bioinformatics 24(5):713-14.
Li et al., 2009, SOAP2: an improved ultrafast tool for short read alignment, Bioinformatics 25(15): 1966-67.
Li et al., 2009, The Sequence Alignment/Map format and SAMtools, Bioinformatics, 2009, 25(16):2078-9.
Li et al., 2011, Single Nucleotide Polymorphism Genotyping and Point Mutation Detection by Ligation on Microarrays, Journal of Nanoscience and Nanotechnology 11(2):994-1003.
Li, 2014, HUGO: Hierarchical mUlti-reference Genome cOmpression for aligned reads, JAMIA 21:363-373.
Lin et al., 2012, Development and evaluation of a reverse dot blot assay for the simultaneous detection of common alpha and beta thalassemia in Chinese, Blood Cells Molecules, and Diseases 48(2):86-90.
Lin, 2008, ZOOM! Zillions of Oligos Mapped, Bioinformatics 24:2431.
Lipman et al., 1985, Rapid and sensitive protein similarity searches, Science 227(4693):1435-41.
Liu et al., 2012, Comparison of next-generation sequencing systems, ePub 2012(251364).
Llopis, 1998, Measurement of cytosolic, mitochondrial, and Golgi pH in single living cells with green fluorescent proteins, Proc Natl Acad Sci USA 95(12):6803-08.
MacArthur, 2014, Guidelines for investigating causality of sequence variaants in human disease, Nature 508:469-76.
Maddalena, 2005, Technical standards and guidelines: molecular genetic testing for ultra-rare disorders, Genet Med 7:571-83.
Malewicz, 2010, Pregel: a system for large-scale graph processing, Proc. ACM SIGMOD Int Conf Mgmt Data 135-46.
Mamanova, 2010, Target-enrichment strategies for nextgeneration sequencing, Nature Methods 7(2):111-8.
Margulies et al., 2005, Genome sequencing in micro-fabricated high-density picoliter reactors, Nature, 437:376-380 (2005).

(56) References Cited

OTHER PUBLICATIONS

Margulies et al., 2005, Genome sequencing in microfabricated high-density picolitre reactors, Nature 437, Supplemental Material, 52 pages.

Marras, 1999, Multiplex detection of single-nucleotide variations using molecular beacons, Genetic Analysis: Biomolecular Engineering 14:151.

Maxam & Gilbert, 1977, A new method for sequencing DNA, PNAS 74:560-564.

May, Robert M., 1988, How Many Species Are There on Earth?, Science 241:1441.

McKenna, 2010, The Genome Analysis Toolkit: a MapReduce framework for analyzing next-generation DNA sequencing data, Genome Res 20(9):1297-1303.

Meyer et al., 2008, Parallel tagged sequencing on the 454 platform, Nature Protocols 3(2):267-78.

Mills et al., 2010, Mapping copy number variation by population-scale genome sequencing, Nature 470:59-65.

Minton et al., 2011, Mutation Surveyor: Software for DNA Sequence Analysis, Methods in Molecular Biology 688:143-53.

Miyazaki et al., 2009, Characterization of deletion breakpoints in patients with dystrophinopathy carrying a deletion of exons 45-55 of the Duchenne muscular dystrophy (DMD) gene, Journal of Human Genetics 54:127-30.

Mockler et al., 2005, Applications of DNA tiling arrays for whole-genome analysis, Genomics 85:1-15.

Mohammed, 2012, DELIMINATE—a fast and efficient methods for loss-less compression of genomice sequences, Bioinformatics 28(19):2527-2529.

Moudrianakis E. N. & Beer M., 1965, Base sequence determination in nucleic acids with the electron microscope, PNAS, 53:564-71.

Mullan, 2002, Multiple sequence alignment-the gateway to further analysis, Brief Bioinform., 3:303-5.

Nan et al., 2006, A novel CFTR mutation found in a Chinese patient with cystic fibrosis, Chinese Medical Journal 119(2):103-9.

Narang et al., 1979, Improved phosphotriester method for the synthesis of gene fragments, Methods Enzymol., 68:90.

* cited by examiner

|  | OLTP | OLAP |
|---|---|---|
| Function | day-to-day operations | decision support |
| DB Design | application-oriented | subject oriented |
| Data | current<br>up-to-date<br>detailed<br>isolated | historical<br>summarized<br>multidimensional<br>consolidated |
| Usage | repetitive | ad hoc |
| Access | read/write | many scans |
| Unit | short transaction | complex query |
| #Records Accessed | tens-hundreds | hundreds-millions |
| Metric | transaction throughput | query yield |
| DB Size | 100MB-GB | 100GB-TB |

FIG. 13

VARIANT DATABASE

CROSS-REFERENCE TO RELATED APPLICATION

This application is a continuation of U.S. patent application Ser. No. 13/667,575, filed Nov. 2, 2012, which application claims priority to and the benefit of Provisional U.S. Patent Application Ser. No. 61/621,779, filed on Apr. 9, 2012, the entire contents of which are incorporated herein by reference.

TECHNICAL FIELD

The invention generally relates to systems and methods for describing genetic variants and polymorphisms.

BACKGROUND INFORMATION

When a child is born suffering from symptoms that are associated with a genetic condition, genetic testing can be very valuable to the child and his or her family. Genetic testing for the child can aid the diagnosis. Genetic testing for the parents can help the parents evaluate risks and factors as the family plans and grows. Hundreds of different genetic tests exist to study many of the 20,000-plus genes and include, in a broader sense, a variety of molecular and biochemical tests.

Lab results from any given genetic test are typically presented to a doctor who then interprets the results for the patient. For example, if the raw results indicate a genetic mutation, the doctor may look up whether that mutation has been reported in the literature. Some mutations are published in databases. These databases typically exist as a "flat file" of genetic sequence data, sometimes organized by gene or by disease.

Searching the literature and database is a laborious process. Any given mutation may have several different common names arising from different studies reported in different publications. Databases provide for electronic lookup but are limited by their flat file structures. For example, each known mutation may be stored as its own row in a table. Medical significance often results from certain combinations of mutations. For example, a single nucleotide polymorphism may only be indicative of a disease when a certain deletion is present on the same chromosome. Flat file gene databases generally have no mechanism for storing information about such combinations. Even where a doctor can find database entries for all of the patient's lab results, the doctor may then have to turn back to the literature to research the pathology of the particular combination of results. Thus, even with existing flat file databases, interpreting the results of genetic tests for patient counseling is a slow and imperfect process.

SUMMARY OF THE INVENTION

The invention generally relates to a system and method for describing genetic variants based on information about variant mutation types and information about relationships among variants. The invention uses object-oriented concepts to store and describe variants and relations among those variants. Genetic information is stored as objects corresponding to known mutations as well as objects corresponding to relations among those mutations. Variant objects and relationship objects are all instances of one abstract class of genomic feature and objects may contain other objects. Since each object can contain any number of other objects, a relation object can contain variant objects that each describe a mutation. Each variant object can be used by many relation objects and new variant objects or relation objects can be added without modifying the existing data structure. Thus, descriptions of many variants can be represented without having to provide a new flat file entry for each new variant. Where a disorder is known to arise from a combination of mutations, disorder-specific information can be associated with the relation object that represents that combination, even where the individual mutations are benign. This way, genetic test results that indicate specific mutations can be used to access corresponding objects to provide a report of variants for a patient. The report can include medical information associated with the combination of mutations in the patient's genome. Since production of the patient report involves accessing the variant objects and relation objects, the patient report can accurately and richly describe the patient's carrier screening results. With such tools, reports can be provided to health professionals, allowing them to counsel patients and families on important health issues.

In one aspect, the invention involves providing a description of genetic variants in a patient's genome within the context of the production of a patient report. After genetic data representing mutations within the individual are received, one or more modules of the invention operate to retrieve, for each mutation, a variant object comprising a description of the mutation. The variant objects are retrieved from storage in a variant database where they are stored as instances of an abstract class of genomic feature. The one or more modules are used to determine a relationship between mutations and retrieve a relation object from the database, which is also an instance of the abstract class of genomic feature. In certain non-limiting embodiments, a results entry module is employed to retrieve the objects and determine relationships and a report production module is employed to provide the report. In some embodiments, the one or more modules operate within an online-transaction processing framework (e.g., the results entry module accessing the objects to enter results, the report production module accessing the variant representations, etc.) to enter results and to deliver the report with a rapid turnaround time.

Using object-oriented concepts, each object (i.e., the variant objects and the variant relation objects) inherits attributes from the abstract class such as, for example, a start position in genomic coordinate space. The objects can be provided by a relational database within a computer-readable storage device. In some embodiments, the production application operates in a production server within an online transaction processing framework, and reads the objects from the storage device, using the objects and associated information to produce a patient report.

Methods of the invention are extensible and new genomic features may be represented as they are introduced or discovered. An object can be used, for example, to represent an exon, intron, gene, open reading frame, epigenetically modified region, methylated sequence, regulatory region, promoter, splice site, protein motif, protein secondary structure, and non-coding region or any other such genomic region. Objects can be variants or variant relations, and variant relation objects can contain any number of objects including variant objects and other variant relation objects. In some embodiments, a variant object contains a description of a mutation, for example, as a systematic name with a numeral representing a distance from a start position, a specification of a mutation type, and one or more IUPAC characters representing nucleotides.

Information can be received from multiple different assay pipelines including, for example, next-generation-sequencing, multi-plex ligation dependent probe amplification analyses, biochemical analyses, or other such analyses. Information can be received that describes a novel mutation and the novel mutation can be included in the patient report. In some embodiments, novel mutations are fed back into the underlying database, either directly, or via a development environment, e.g., to be curated by geneticists. Novel mutation information can be stored in the database in the storage device for immediate inclusion or to be curated in a later stage.

In a related aspect, the invention provides a system for providing a description of variants in a patient's genome, the system having a processor and a computer-readable storage device. Stored instructions, when executed, cause the processor to receive genetic data representing mutations in an individual, retrieve from a database a first object with a description of a first mutation as a variant of a reference and a second object, itself having a description of the second mutation. The processor can determine a relationship between the mutations, and retrieve a third object including a description of the relationship. Each object is an instance of an abstract class of genomic feature and receives, via object oriented concepts relating to inheritance and polymorphisms, attributes of the abstract class. Use of these objects and concepts allows the system to represent a wide variety of different genomic constructs within a very simple and extensible design. This allows the system to provide variant reports with rich levels of semantic information for those genomic constructs within rapid turnaround times.

The production of patient reports according to embodiments of the invention draws upon a database of genetic information. Accordingly, aspects of the invention provide systems and methods for the use and development of a database.

In another aspect, the invention provides methods for building a database of variant descriptions by using a computer to provide an abstract class of genomic feature object. Mutations are described by creating variant objects as instances of the abstract class. Relations among mutations are described by creating variant relation objects, also instances of the abstract class. A variant relation object is itself a subclass of variant and further may contain one or more variants, including other variant relations. Descriptions of variants are represented in the database by objects such as one or more of the variant relation objects. As each object is an instance of the abstract class of genomic feature, each object inherits attributes from that class such as, for example, start position in genomic coordinate space. Using object-oriented concepts of polymorphism and composition, a relation object can be described as having one or more other objects (e.g., having a "has-a" relationship to other objects). Under these concepts, objects can be described as instances of the abstract class (e.g., having an "is-a" relationship to the abstract class).

Methods of constructing the database are provided that accommodate complex information. For example, additional variants can be added by creating new variant objects and additional relations can be added by creating new variant relation objects. Methods of the invention can be used to provide a relational database, for example, stored within a computer-readable storage device. Objects within the database can be branded with information showing the database version in which they appear. Methods further include releasing the branded objects to the production environment. Thus is provided a database that, when released to production, can be used to provide patient reports that include information pointing back to the database version upon which they were based.

In some embodiments, new versions of the database replace or supplement previous versions. For example, a database may include objects with description made in reference to human genome build 18 (hg18) and a subsequent database may be based on hg19. In certain embodiments however, a new version of the database includes the addition of new data to an existing version without overriding or modifying the existing version. In fact, extensibility is a hallmark of the methods and systems of the invention. For example, new types of genomic features, not yet included in the database, may be added without disrupting or changing the existing database contents.

In a related aspect, the invention provides systems for building a database of variant descriptions by using a computer to provide an abstract class of genomic feature object. Systems of the invention include a computer processor operable to create variant objects, each variant object being an instance of an abstract class of genomic feature object and including a description of a mutation. Each object can be stored in a computer storage device including a tangible, non-transitory, computer-readable medium. The processor is further operable to create relation objects. Each relation object is an instance of the abstract class of genomic feature object and may contain one or more genomic feature objects as well as a description of a relationship among the one or more genomic feature objects. Systems of the invention can then provide descriptions of variants based on at least one of the relation objects.

BRIEF DESCRIPTION OF THE DRAWINGS

FIG. 13 shows features of on-line transaction processing and on-line analytical processing embodiments of the invention.

DESCRIPTION

Figure 1:
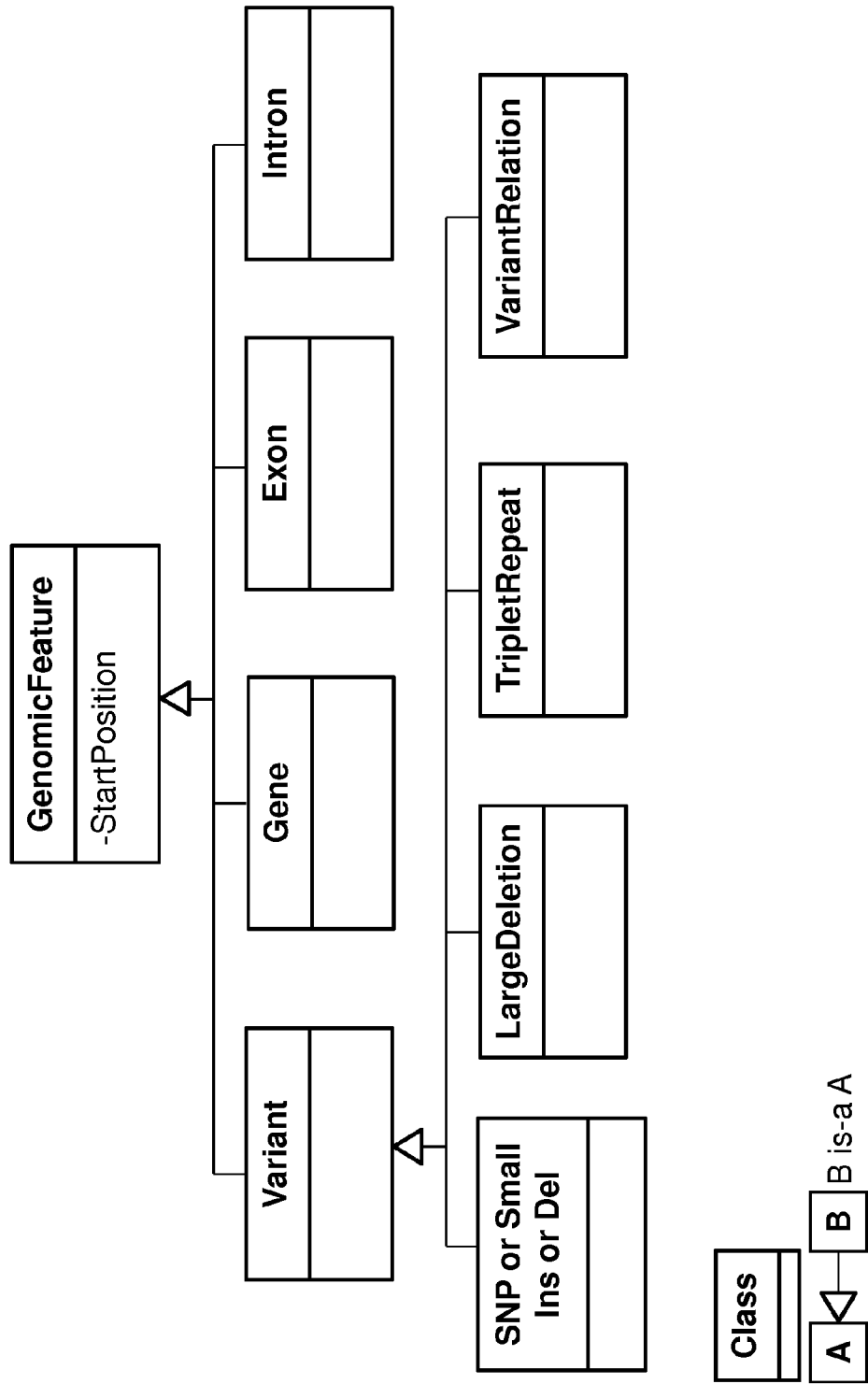
FIG. 1 is a diagram modeling database design according to certain embodiments.

The invention generally relates to systems and methods for reporting genetic variants. Embodiments of the invention provide a database and interface application for use in a clinical environment to analyze genetic test results and produce a report describing a patient's genetic variants and their medical significance. The invention further includes systems and methods for developing a database of genetic information for use in production and research applications. In production, the invention can use an online transaction processing framework to access the database in real time to produce the patient report. Accurate and specific real-time transactions according to the invention allow for genetic testing, results analysis, and reporting with good turn around time (TAT), which supports medical practices to help treat patients in a cost-effective way.

Examining a patient may include ordering one or more genetic tests to obtain test results to be used in diagnosis and counseling. The invention may operate with any suitable results from genetic testing or with any genetic information format known in the art including, for example, results obtained from laboratory tests or from family history information. In certain embodiments, results are obtained by genetic testing.

Genetic testing, including DNA-based tests, involves techniques used to test for genetic disorders through the direct examination of nucleic acids. Other genetic tests include biochemical tests for such gene products as enzymes and other proteins and for microscopic examination of stained or fluorescent chromosomes.

Genetic tests may be used in a variety of circumstances or for a variety of purposes. For example, genetic testing includes carrier screening to identify unaffected individuals who carry one copy of a gene for a disease with a homozygous recessive genotype. Genetic testing can further include pre-implantation genetic diagnosis, prenatal diagnosis, newborn screening, genealogical testing, screening and risk-assessment for adult-onset disorders such as Huntington's, cancer or Alzheimer's disease, as well as forensic and identity testing.

Testing is sometimes used just after birth to identify genetic disorders that can be treated early in life. Newborn tests include tests for phenylketonuria and congenital hypothyroidism.

Genetic tests can be used to diagnose genetic or chromosomal conditions at any point in a person's life, to rule out or confirm a diagnosis. Carrier testing is used to identify people who carry one copy of a gene mutation that, when present in two copies, causes a genetic disorder. Prenatal testing is used to detect changes in a fetus's genes or chromosomes before birth.

Predictive testing is used to detect gene mutations associated with disorders that appear later in life. For example, testing for a mutation in BRCA1 can help identify people at risk for breast cancer. Pre-symptomatic testing can help identify those at risk for hemochromatosis.

Genetic testing further plays important roles in research. Researchers use existing lab techniques, as well as develop new ones, to study known genes, discover new genes, and understand genetic conditions.

At present, there are more than 1,000 different genetic tests available. Genetic tests can be performed using a biological sample such as blood, hair, skin, amniotic fluid, cheek swabs from a buccal smear, or other biological materials. Blood samples can be collected via syringe or through a finger-prick or heel-prick. Such biological samples are typically processed and sent to a laboratory. A number of genetic tests can be performed, including karyotyping, restriction fragment length polymorphism (RFLP) tests, biochemical tests, mass spectrometry tests such as tandem mass spectrometry (MS/MS), tests for epigenetic phenomenon such as patterns of nucleic acid methylation, and nucleic acid hybridization tests such as fluorescent in-situ hybridization. In certain embodiments, a nucleic acid is isolated and sequenced.

Nucleic acid template molecules (e.g., DNA or RNA) can be isolated from a sample containing other components, such as proteins, lipids and non-template nucleic acids. Nucleic acid can be obtained directly from a patient or from a sample such as blood, urine, cerebrospinal fluid, seminal fluid, saliva, sputum, stool and tissue. Any tissue or body fluid specimen may be used as a source for nucleic acid. Nucleic acid can also be isolated from cultured cells, such as a primary cell culture or a cell line. Generally, nucleic acid can be extracted, isolated, amplified, or analyzed by a variety of techniques such as those described by Green and Sambrook, Molecular Cloning: A Laboratory Manual (Fourth Edition), Cold Spring Harbor Laboratory Press, Woodbury, N.Y. 2,028 pages (2012); or as described in U.S. Pat. No. 7,957,913; U.S. Pat. No. 7,776,616; U.S. Pat. No. 5,234,809; U.S. Pub. 2010/0285578; and U.S. Pub. 2002/0190663.

Nucleic acid obtained from biological samples may be fragmented to produce suitable fragments for analysis. Template nucleic acids may be fragmented or sheared to desired length, using a variety of mechanical, chemical and/or enzymatic methods. Nucleic acid may be sheared by sonication, brief exposure to a DNase/RNase, hydroshear instrument, one or more restriction enzymes, transposase or nicking enzyme, exposure to heat plus magnesium, or by shearing. RNA may be converted to cDNA, e.g., before or after fragmentation. In one embodiment, nucleic acid from a biological sample is fragmented by sonication. Generally, individual nucleic acid template molecules can be from about 2 kb bases to about 40 kb, e.g., 6 kb-10 kb fragments.

A biological sample as described herein may be lysed, homogenized, or fractionated in the presence of a detergent or surfactant. The concentration of the detergent in the buffer may be about 0.05% to about 10.0%, e.g., 0.1% to about 2%. The detergent, particularly a mild one that is non-denaturing, can act to solubilize the sample. Detergents may be ionic (e.g., deoxycholate, sodium dodecyl sulfate (SDS), N-lauroylsarcosine, and cetyltrimethylammonium bromide) or nonionic (e.g., octyl glucoside, polyoxyethylene(9)dodecyl ether, digitonin, polysorbate 80 such as that sold under the trademark TWEEN by Uniqema Americas (Paterson, N.J.), $(C_{14}H_{22}O(C_2H_4)_n)$ sold under the trademark TRITON X-100 by Dow Chemical Company (Midland, Mich.), polidocanol, n-dodecyl beta-D-maltoside (DDM), or NP-40 nonylphenyl polyethylene glycol). A zwitterionic reagent may also be used in the purification schemes, such as zwitterion 3-14 and 3-[(3-cholamidopropyl)dimethyl-ammonio]-1-propanesulfonate (CHAPS). Urea may also be added. Lysis or homogenization solutions may further contain other agents, such as reducing agents. Examples of such reducing agents include dithiothreitol (DTT), β-mercaptoethanol, dithioerythritol (DTE), glutathione (GSH), cysteine, cysteamine, tricarboxyethyl phosphine (TCEP), or salts of sulfurous acid.

In various embodiments, the nucleic acid is amplified, for example, from the sample or after isolation from the sample. Amplification refers to production of additional copies of a nucleic acid sequence and is generally carried out using polymerase chain reaction (PCR) or other technologies known in the art. The amplification reaction may be any amplification reaction known in the art that amplifies nucleic acid molecules, such as PCR, nested PCR, PCR-single strand conformation polymorphism, ligase chain reaction (Barany, F., The Ligase Chain Reaction in a PCR World, Genome Research, 1:5-16 (1991); Barany, F., Genetic disease detection and DNA amplification using cloned thermostable ligase, PNAS, 88:189-193 (1991); U.S. Pat. No. 5,869,252; and U.S. Pat. No. 6,100,099), strand displacement amplification and restriction fragments length polymorphism, transcription based amplification system, rolling circle amplification, and hyper-branched rolling circle amplification. Further examples of amplification techniques that can be used include, but are not limited to, quantitative PCR, quantitative fluorescent PCR (QF-PCR), multiplex fluorescent PCR (MF-PCR), real time PCR (RTPCR), restriction fragment length polymorphism PCR (PCR-RFLP), in situ rolling circle amplification (RCA), bridge PCR, picotiter PCR, emulsion PCR, transcription amplification, self-sustained sequence replication, consensus sequence primed PCR, arbitrarily primed PCR, degenerate oligonucleotide-primed PCR, and nucleic acid based sequence amplification (NABSA). Amplification methods that can be used include those described in U.S. Pats. 5,242,794; 5,494,810; 4,988,617; and 6,582,938. In certain embodiments, the amplification reaction is PCR as described, for example, in Dieffenbach and Dveksler, PCR Primer, a Laboratory Manual, 2nd Ed, 2003, Cold Spring Harbor Press, Plainview, N.Y.; U.S. Pat. No. 4,683,195; and U.S. Pat. No. 4,683,202, hereby incorporated by reference. Primers for PCR, sequencing, and other methods can be prepared by cloning, direct chemical synthesis, and other methods known in the art. Primers can also be obtained from commercial sources such as Eurofins MWG Operon (Huntsville, Ala.) or Life Technologies (Carlsbad, Calif.).

With these methods, a single copy of a specific target nucleic acid may be amplified to a level that can be detected by several different methodologies (e.g., sequencing, staining, hybridization with a labeled probe, incorporation of biotinylated primers followed by avidin-enzyme conjugate detection, or incorporation of 32P-labeled dNTPs). Further, the amplified segments created by an amplification process such as PCR are, themselves, efficient templates for subsequent PCR amplifications. After any processing steps (e.g., obtaining, isolating, fragmenting, or amplification), nucleic acid can be sequenced.

Sequencing may be by any method known in the art. DNA sequencing techniques include classic dideoxy sequencing reactions (Sanger method) using labeled terminators or primers and gel separation in slab or capillary, sequencing by synthesis using reversibly terminated labeled nucleotides, pyrosequencing, 454 sequencing, Illumina/Solexa sequencing, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, polony sequencing, and SOLiD sequencing. Separated molecules may be sequenced by sequential or single extension reactions using polymerases or ligases as well as by single or sequential differential hybridizations with libraries of probes.

A sequencing technique that can be used includes, for example, use of sequencing-by-synthesis systems sold under the trademarks GS JUNIOR, GS FLX+ and 454 SEQUENCING by 454 Life Sciences, a Roche company (Branford, Conn.), and described by Margulies, M. et al., Genome sequencing in micro-fabricated high-density picotiter reactors, Nature, 437:376-380 (2005); U.S. Pat. No. 5,583,024; U.S. Pat. No. 5,674,713; and U.S. Pat. No. 5,700,673, the contents of which are incorporated by reference herein in their entirety. 454 sequencing involves two steps. In the first step of those systems, DNA is sheared into fragments of approximately 300-800 base pairs, and the fragments are blunt ended. Oligonucleotide adaptors are then ligated to the ends of the fragments. The adaptors serve as primers for amplification and sequencing of the fragments. The fragments can be attached to DNA capture beads, e.g., streptavidin-coated beads using, e.g., Adaptor B, which contains 5'-biotin tag. The fragments attached to the beads are PCR amplified within droplets of an oil-water emulsion. The result is multiple copies of clonally amplified DNA fragments on each bead. In the second step, the beads are captured in wells (pico-liter sized). Pyrosequencing is performed on each DNA fragment in parallel. Addition of one or more nucleotides generates a light signal that is recorded by a CCD camera in a sequencing instrument. The signal strength is proportional to the number of nucleotides incorporated. Pyrosequencing makes use of pyrophosphate (PPi) which is released upon nucleotide addition. PPi is converted to ATP by ATP sulfurylase in the presence of adenosine 5' phosphosulfate. Luciferase uses ATP to convert luciferin to oxyluciferin, and this reaction generates light that is detected and analyzed.

Another example of a DNA sequencing technique that can be used is SOLiD technology by Applied Biosystems from Life Technologies Corporation (Carlsbad, Calif.). In SOLiD sequencing, genomic DNA is sheared into fragments, and adaptors are attached to the 5' and 3' ends of the fragments to generate a fragment library. Alternatively, internal adaptors can be introduced by ligating adaptors to the 5' and 3' ends of the fragments, circularizing the fragments, digesting the circularized fragment to generate an internal adaptor, and attaching adaptors to the 5' and 3' ends of the resulting fragments to generate a mate-paired library. Next, clonal bead populations are prepared in microreactors containing beads, primers, template, and PCR components. Following PCR, the templates are denatured and beads are enriched to separate the beads with extended templates. Templates on the selected beads are subjected to a 3' modification that permits bonding to a glass slide. The sequence can be determined by sequential hybridization and ligation of partially random oligonucleotides with a central determined base (or pair of bases) that is identified by a specific fluorophore. After a color is recorded, the ligated oligonucleotide is removed and the process is then repeated.

Another example of a DNA sequencing technique that can be used is ion semiconductor sequencing using, for example, a system sold under the trademark ION TORRENT by Ion Torrent by Life Technologies (South San Francisco, Calif.). Ion semiconductor sequencing is described, for example, in Rothberg, et al., An integrated semiconductor device enabling non-optical genome sequencing, Nature 475:348-352 (2011); U.S. Pubs. 2009/0026082, 2009/0127589, 2010/0035252, 2010/0137143, 2010/0188073, 2010/0197507, 2010/0282617, 2010/0300559, 2010/0300895, 2010/0301398, and 2010/0304982, the content of each of which is incorporated by reference herein in its entirety. In ion semiconductor sequencing, DNA is sheared into fragments of approximately 300-800 base pairs, and the fragments are blunt ended. Oligonucleotide adaptors are then ligated to the ends of the fragments. The adaptors serve as primers for amplification and sequencing of the fragments. The fragments can be attached to a surface and are attached at a resolution such that the fragments are individually resolvable. Addition of one or more nucleotides releases a proton ($H^+$), which signal is detected and recorded in a sequencing instrument. The signal strength is proportional to the number of nucleotides incorporated.

Another example of a sequencing technology that can be used is Illumina sequencing. Illumina sequencing is based on the amplification of DNA on a solid surface using fold-back PCR and anchored primers. Genomic DNA is fragmented, and adapters are added to the 5' and 3' ends of the fragments.

DNA fragments that are attached to the surface of flow cell channels are extended and bridge amplified. The fragments become double stranded, and the double stranded molecules are denatured. Multiple cycles of the solid-phase amplification followed by denaturation can create several million clusters of approximately 1,000 copies of single-stranded DNA molecules of the same template in each channel of the flow cell. Primers, DNA polymerase and four fluorophore-labeled, reversibly terminating nucleotides are used to perform sequential sequencing. After nucleotide incorporation, a laser is used to excite the fluorophores, and an image is captured and the identity of the first base is recorded. The 3' terminators and fluorophores from each incorporated base are removed and the incorporation, detection and identification steps are repeated. Sequencing according to this technology is described in U.S. Pub. 2011/0009278, U.S. Pub. 2007/0114362, U.S. Pub. 2006/0024681, U.S. Pub. 2006/0292611, U.S. Pat. No. 7,960,120, U.S. Pat. No. 7,835,871, U.S. Pat. No. 7,232,656, U.S. Pat. No. 7,598,035, U.S. Pat. No. 6,306,597, U.S. Pat. No. 6,210,891, U.S. Pat. No. 6,828,100, U.S. Pat. No. 6,833,246, and U.S. Pat. No. 6,911,345, each of which are herein incorporated by reference in their entirety.

Another example of a sequencing technology that can be used includes the single molecule, real-time (SMRT) technology of Pacific Biosciences (Menlo Park, Calif.). In SMRT, each of the four DNA bases is attached to one of four different fluorescent dyes. These dyes are phospholinked. A single DNA polymerase is immobilized with a single molecule of template single stranded DNA at the bottom of a zero-mode waveguide (ZMW). A ZMW is a confinement structure which enables observation of incorporation of a single nucleotide by DNA polymerase against the background of fluorescent nucleotides that rapidly diffuse in and out of the ZMW (in microseconds). It takes several milliseconds to incorporate a nucleotide into a growing strand. During this time, the fluorescent label is excited and produces a fluorescent signal, and the fluorescent tag is cleaved off. Detection of the corresponding fluorescence of the dye indicates which base was incorporated. The process is repeated.

Another example of a sequencing technique that can be used is nanopore sequencing (Soni, G. V., and Meller, A., Clin Chem 53: 1996-2001 (2007)). A nanopore is a small hole, of the order of 1 nanometer in diameter. Immersion of a nanopore in a conducting fluid and application of a potential across it results in a slight electrical current due to conduction of ions through the nanopore. The amount of current which flows is sensitive to the size of the nanopore. As a DNA molecule passes through a nanopore, each nucleotide on the DNA molecule obstructs the nanopore to a different degree. Thus, the change in the current passing through the nanopore as the DNA molecule passes through the nanopore represents a reading of the DNA sequence.

Another example of a sequencing technique that can be used involves using a chemical-sensitive field effect transistor (chemFET) array to sequence DNA (for example, as described in U.S. Pub. 2009/0026082). In one example of the technique, DNA molecules can be placed into reaction chambers, and the template molecules can be hybridized to a sequencing primer bound to a polymerase. Incorporation of one or more triphosphates into a new nucleic acid strand at the 3' end of the sequencing primer can be detected by a change in current by a chemFET. An array can have multiple chemFET sensors. In another example, single nucleic acids can be attached to beads, and the nucleic acids can be amplified on the bead, and the individual beads can be transferred to individual reaction chambers on a chemFET array, with each chamber having a chemFET sensor, and the nucleic acids can be sequenced.

Another example of a sequencing technique that can be used involves using a electron microscope as described, for example, by Moudrianakis, E. N. and Beer M., in Base sequence determination in nucleic acids with the electron microscope, III. Chemistry and microscopy of guanine-labeled DNA, PNAS 53:564-71 (1965). In one example of the technique, individual DNA molecules are labeled using metallic labels that are distinguishable using an electron microscope. These molecules are then stretched on a flat surface and imaged using an electron microscope to measure sequences.

Sequencing generates a plurality of reads. Reads generally include sequences of nucleotide data less than about 150 bases in length, or less than about 90 bases in length. In certain embodiments, reads are between about 80 and about 90 bases in length, e.g., about 85 bases in length. In some embodiments, these are very short reads, i.e., less than about 50 or about 30 bases in length. After obtaining sequence reads, they can be assembled into sequence assemblies. Sequence assembly can be done by methods known in the art including reference-based assemblies, de novo assemblies, assembly by alignment, or combination methods. Assembly can include methods described in U.S. Pat. No. 8,209,130 titled Sequence Assembly, and co-pending U.S. patent application Ser. No. 13/494,616, both by Porecca and Kennedy, the contents of each of which are hereby incorporated by reference in their entirety for all purposes. In some embodiments, sequence assembly uses the low coverage sequence assembly software (LOCAS) tool described by Klein, et al., in LOCAS-A low coverage sequence assembly tool for re-sequencing projects, PLoS One 6(8) article 23455 (2011), the contents of which are hereby incorporated by reference in their entirety. Sequence assembly is described in U.S. Pat. No. 8,165,821; U.S. Pat. No. 7,809,509; U.S. Pat. No. 6,223,128; U.S. Pub. 2011/0257889; and U.S. Pub. 2009/0318310, the contents of each of which are hereby incorporated by reference in their entirety.

Nucleic acid sequencing, assembly, and analysis is but one assay pipeline of information compatible with the invention. The invention includes systems and methods that can use one or more different assay pipelines for genetic analysis. The invention further includes systems and methods adapted to operate with changing assay pipelines—i.e., certain pipelines may, over time, cease to be used in systems and methods of the invention, new assay pipelines may be introduced, suspended assay pipelines may be re-introduced, and existing assay pipelines may be transformed or repurposed as technology or demand changes. Nucleic acid sequencing embraces a plurality of different assay pipelines including those discussed above. The analytical targets of individual assay pipelines may overlap or not. For example, certain assay pipelines may be used to study one aspect of genetic information and a different assay pipeline may be used to re-study that aspect or to confirm a prior study (e.g., sequencing by Sanger dideoxy chain termination can complement Illumina sequencing). Other assay pipelines for use with the invention include those suitable for use with the aims and methodologies described herein, such as the multiplex ligation-dependent probe amplification systems sold under the trademark MLPA by MRC-Holland (Amsterdam, the Netherlands), triplet-PCR, or other genotyping techniques.

Multiplex ligation-dependent probe amplification (MLPA) uses a pair of primer probe oligos, in which each oligo of the pair has a hybridization portion and a fluorescently-labeled primer portion. When the two oligos hybridize adjacent to each other on the target sequence, they are ligated by a ligase. The primer portions are then used to amplify the ligated probes. Resulting product is separated by electrophoresis, and the presence of fluorescent label at positions indicting the presence of target in the sample is detected. Using a single set of primers and hybridization portions for multiple targets, the analysis can be multiplexed. Such techniques can be used for quantitative detection of genomic deletions, duplications and point mutations. Multiplex ligation-dependent probe amplification discriminates sequences that differ even by a single nucleotide and can be used to detect known mutations. Methods for use in multiplex ligation-dependent amplification are described in Yau S C, et al., Accurate diagnosis of carriers of deletions and duplications in Duchenne/Becker muscular dystrophy by fluorescent dosage analysis, J Med Genet. 33(7):550-558 (1996); Procter M, et al., Molecular diagnosis of Prader-Willi and Angelman syndromes by methylation-specific melting analysis and methylation-specific multiplex ligation-dependent probe amplification, Clin Chem 52(7): 1276-1283 (2006); Bunyan D J, et al., Dosage analysis of cancer predisposition genes by multiplex ligation-dependent probe amplification, Br J Cancer 91(6):1155-1159 (2004); U.S. Pub. 2012/0059594; U.S. Pub. 2009/0203014; U.S. Pub. 2007/0161013; U.S. Pub. 2007/0092883; and U.S. Pub. 2006/0078894, the contents of which are hereby incorporated by reference in their entirety.

In some embodiments, assay pipelines make use of the triplet repeat primed PCR (TP-PCR) method to test for variant alleles. TP-PCR was developed to screen for expanded alleles in myotonic dystrophy as discussed in Warner J. P., et al., A general method for the detection of large CAG repeat expansions by fluorescent PCR, J Med Genet. 33(12):1022-1026 (1996). The PCR assay uses fluorescently labeled primer pairs in which one sits by a repeat and the other sits at any of multiple, repeated sites within a repeat. The results give a fluorescence trace ladder showing pathogenic repeats that cannot be amplified using flanking primers. TP-PCR is discussed in Ciotti, et al., Triplet repeat primed PCR (TP PCR) in molecular diagnostic testing for Friedreich ataxia, J Mol Diagn 6(4):285-289 (2004).

In certain embodiments, assay pipelines include restriction mapping analysis. With this method genomic DNA is digested with a restriction enzyme and analyzed on an electrophoresis gel or with a Southern blot to determine the presence or absence of a polymorphism that changes the recognition site for the restriction enzyme. This method can also be used to determine the presence or absence of SNP or indel variants by observing the lengths of the resulting DNA fragments. Restriction analysis is discussed in U.S. Pub. 2007/0042369.

Other assay pipelines include methods for detecting genetic markers at a site known to be associated with a genetic condition. Genetic markers can be detected using various tagged oligonucleotide hybridization technologies using, for example, microarrays or other chip-based or bead-based arrays. In some embodiments, a sample from an individual is tested simultaneously for multiple (e.g., thousands) genetic markers. Microarray analysis allows for the detection of abnormalities at a high level of resolution. An array such as an SNP array allows for increased resolution to detect copy number changes while also allowing for copy neutral detection (for both uniparental disomy and consanguinity). Detecting variants through arrays or marker hybridization is discussed, for example, in Schwartz, S., Clinical utility of single nucleotide polymorphism arrays, Clin Lab Med 31(4):581-94 (2011); Li, et al., Single nucleotide polymorphism genotyping and point mutation detected by ligation on microarrays, J Nanosci Nanotechnol 11(2):994-1003 (2011). Reverse dot blot arrays can be used to detect autosomal recessive disorders such as thalassemia and provide for genotyping of wild-type and thalassemia DNA using chips on which allele-specific oligonucleotide probes are immobilized on membrane (e.g., nylon). Assay pipelines can include array-based tests such as those described in Lin, et al., Development and evaluation of a reverse dot blog assay for the simultaneous detection of common alpha and beta thalassemia in Chinese, Blood Cells Mol Dis 48(2):86-90 (2012); Jaijo, et al., Microarray-based mutation analysis of 183 Spanish families with Usher syndrome, Invest Ophthalmol Vis Sci 51(3):1311-7 (2010); and Oliphant A. et al., BeadArray technology: enabling an accurate, cost-effective approach to high-throughput genotyping, Biotechniques Suppl: 56-8, 60-1 (2002). DNA arrays in genetic diagnostics are discussed further in Yoo, et al., Applications of DNA microarray in disease diagnostics, J Microbiol Biotechnol 19(7):635-46 (2009); U.S. Pat. No. 6,913,879; U.S. Pub. 2012/0179384; and U.S. Pub. 2010/0248984, the contents of which are hereby incorporated by reference in their entirety.

Any assay pipeline can be initiated. For example, a variant (e.g., an SNP or indel) can be identified using oligonucleotide ligation assay in which two probes are hybridized over an SNP and are ligated only if identical to the target DNA, one of which has a 3' end specific to the target allele. The probes are only hybridized in the presence of the target. Product is detected by gel electrophoresis, MALDI-TOF mass spectrometry, or by capillary electrophoresis. This assay has been used to report 11 unique cystic fibrosis alleles. Schwartz, et al., Identification of cystic fibrosis variants by polymerase chain reaction/oligonucleotide ligation assay, J Mol Diag 11(3):211-215 (2009). Oligonucleotide ligation assay for use in pipelines is described further in U.S. Pub. 2008/0076118 and U.S. Pub. 2002/0182609, the contents of which are hereby incorporated by reference in their entirety.

Assay pipelines generally provide results that include a description of a patient's genetic information. That information can be an identification of a mutation, or variant, of a known gene or other genetic region. For example, in some embodiments, result information includes a sequence listing of part of a patient's genes. In certain embodiments, the results are provided as, for example, a gene sequence file (e.g., a FASTA file).

In some embodiments, results are provided according to a systematic nomenclature. For example, a variant can be described by a systematic comparison to a specified reference which is assumed to be unchanging and identified by a unique label such as a name or accession number. For a given gene, coding region, or open reading frame, the A of the ATG start codon is denoted nucleotide +1 and the nucleotide 5' to +1 is −1 (there is no zero). A lowercase g, c, or m prefix, set off by a period, indicates genomic DNA, cDNA, or mitochondrial DNA, respectively.

A systematic name can be used to describe a number of variant types including, for example, substitutions, deletions, insertions, and variable copy numbers. A substitution name starts with a number followed by a "from to" markup. Thus, 199A>G shows that at position 199 of the reference sequence, A is replaced by a G. A deletion is shown by "del" after the number. Thus 223delT shows the deletion of T at nt 223 and 997-999del shows the deletion of three nucleotides (alternatively, this mutation can be denoted as 997-999delTTC). In short tandem repeats, the 3' nt is arbitrarily assigned; e.g. a TG deletion is designated 1997-1998delTG or 1997-1998del (where 1997 is the first T before C). Insertions are shown by ins after an interval. Thus 200-201insT denotes that T was inserted between nts 200 and 201. Variable short repeats appear as 997(GT)N-N'. Here, 997 is the first nucleotide of the dinucleotide GT, which is repeated N to N' times in the population.

Variants in introns can use the intron number with a positive number indicating a distance from the G of the invariant donor GU or a negative number indicating a distance from an invariant G of the acceptor site AG. Thus, IVS3+1C>T shows a C to T substitution at nt +1 of intron 3. In any case, cDNA nucleotide numbering may be used to show the location of the mutation, for example, in an intron. Thus, c.1999+1C>T denotes the C to T substitution at nt +1 after nucleotide 1997 of the cDNA. Similarly, c.1997-2A>C shows the A to C substitution at nt −2 upstream of nucleotide 1997 of the cDNA. When the full length genomic sequence is known, the mutation can also be designated by the nt number of the reference sequence.

Relative to a reference, a patient's genome may vary by more than one mutation, or by a complex mutation that is describable by more than one character string or systematic name. The invention further provides systems and methods for describing more than one variant using a systematic name. For example, two mutations in the same allele can be listed within brackets as follows: [1997G>T; 2001A>C]. Systematic nomenclature is discussed in Antonarakis and the Nomenclature Working Group, Recommendations for a nomenclature system for human gene mutations, Human Mutation 11:1-3 (1998).

Assay pipelines produce data that represent one or more mutations. These data are received and a computer application can be used to process the data, determine the relationships among the variants, and to prepare a patient report. The computer application can produce the report by making use of a variant database. As described herein, a variant database according to the invention can include medical information for reporting that is associated with variants, relationships among variants, or both. The computer application produces the report in a transaction that includes accessing those database records that are indicated by the processed, interpreted pipeline results.

A variant database according to the invention allows for rapid transaction turn-around-times for patient report production by employing a novel structure to store and describe variants. In accordance with the invention, individual variants are stored and relationships among variants are stored that use the related variants without needing to duplicate or modify the stored variants.

FIG. 1 shows a design for using object-oriented concepts to implement embodiments of the invention. As shown in FIG. 1, information about variants and relations among them can be represented within the framework of an object-oriented infrastructure. A production application can use object-oriented techniques to describe variants based on use of object entries in an underlying production database having an object-oriented design and corresponding relational database schema. Using such techniques, systems and methods of the invention can adapt to include new genomic features and annotations without disrupting existing content stored as instance data in the database. The design of the variant database according to the invention allows for the representation of a wide variety of genomic features and annotations, in a structure that is extensible and capable of representing deep semantic interconnections between genomic features and corresponding annotations.

In certain embodiments, the invention uses the object-oriented principles of abstraction, inheritance, polymorphism, and containment. For example, the invention uses abstraction to represent nearly every feature of a chromosome as an abstract class of genomic feature. The abstract class of genomic feature can be created having one or more attributes or operations (sometimes called methods). For example, in some embodiments, as shown in FIG. 1, genomic feature is an abstract class of object with a Start Position attribute. The abstract class of genomic feature can also optionally include an end position. These attributes are simply a start position and an optional end position for a chromosome on a given genomic assembly (e.g., hg18). Each subclass of genomic feature inherits those methods or attributes from any superclass. However, each subclass, as a class, can be imbued with methods or attributes unique to that subclass. Accordingly, different subclasses can be used to represent different categories of different genomic features.

Among subclasses of a superclass, the different attributes or methods of the different subclasses confer polymorphic properties on the subclasses. For example, exon and intron may each be a subclass of genomic feature (and instances of each may be contained by a gene subclass—the containment relation is not pictured in FIG. 1), and an exon may have a method to predict protein domains or secondary structure based on known motifs where an intron would not have such a method.

As shown in FIG. 1, inheritance is provided by the "is-a" relationship among levels of class. Each class of object has what is known as an "is-a" relationship to the object depicted above it in the hierarchy shown in FIG. 1. In general, when one object has an is-a relationship with another (when the object is-a subclass of the superclass), all instances of the object have the methods and attributes of the parent (unless overridden). Inheritance, polymorphism, and composition is discussed in Weisfeld, The Object-Oriented Thought Process, Third Edition, Addison-Wesley, Upper Saddle River, N.J. (2012).

In certain embodiments, object-oriented concepts of composition are used to provide descriptions of variants. An insight of the invention is that, while many classes of genomic features can be described by an "is-a" relationship to a superclass (e.g., an exon is a genomic feature, a gene is a genomic feature, GH1 is a gene), some genomic features are suited to being described through a "has-a" relationship. For example, the GH1 gene has 5 exons and 4 introns and could be described as a gene object containing 5 exon objects and 4 intron objects. Note here that, since the gene is contained in a chromosome genomic feature object, the exon and intron objects are thus also contained in the chromosome genomic feature object. (Further note that an object can be contained in, or had by, multiple objects. For example, if it is desired to describe a gene cloned into a plasmid, a plasmid genomic feature object can contain the gene object without disturbing the containment of that gene object by a chromosomal gene object.) Thus the invention uses composition or containment relationships (i.e., "has-a" relationships) along with the is-a hierarchy to produce multiple levels of ownership relationships.

Embodiments of the invention implement a three-level supertype-subtype hierarchy, as shown in FIG. 1. At the top of the hierarchy is genomic feature. Genomic feature is an abstract superclass (i.e., there would never be any standalone instance of genomic feature without a subtype). The second level provides subtypes of genomic feature such as, for example, variant, gene, intron, exon, pseudogene, splice site, etc. This level may be extended as required with new subtypes. The third level includes subtypes of variant. Like genomic feature, variant is also an abstract supertype—there are no instances of variant without one of its subtypes. Note that it is an artifact of the object-relational mapping as to how the conceptual objects are mapped to physical tables. Tables can be stored in a tangible, non-transitory computer readable medium such that the tables embody the hierarchy as depicted in the figures herein. However, these are non-limiting illustrations and other embodiments are within the scope of the invention.

In certain embodiments, each level of the hierarchy may be represented by a corresponding table, and those tables can be joined by parent-child one-to-one relationships through foreign keys. Thus, in some embodiments, genomic feature, variant, and SNPandSmallInsOrDel (for single nucleotide polymorphism (SNP) or a small insertion or deletion) exist as three separate tables that are joined by parent-child one-to-one relationships through foreign keys. The actual physical mappings can be various and other table to data mappings are within the scope of the invention.

Since variant is a supertype, it can have attributes and methods specific to variants and how they relate to other objects. For example, the variant class can have an alias attribute so that each object that is a variant has an alias attribute. The alias attribute can be used to capture names for variants, such as the common descriptive names reported in the literature. Further, the variant class can contain attributes related to medical significance or pathogenicity (e.g., pathogenic, predicted pathogenic, etc.) and supporting references to supporting literature to be drawn on in providing evidence for, and supporting, the patient report produced by systems and methods of the invention.

One feature of the design is provided by making the variant relation a subtype of variant such that each variant relation is-a variant.

Figure 2:
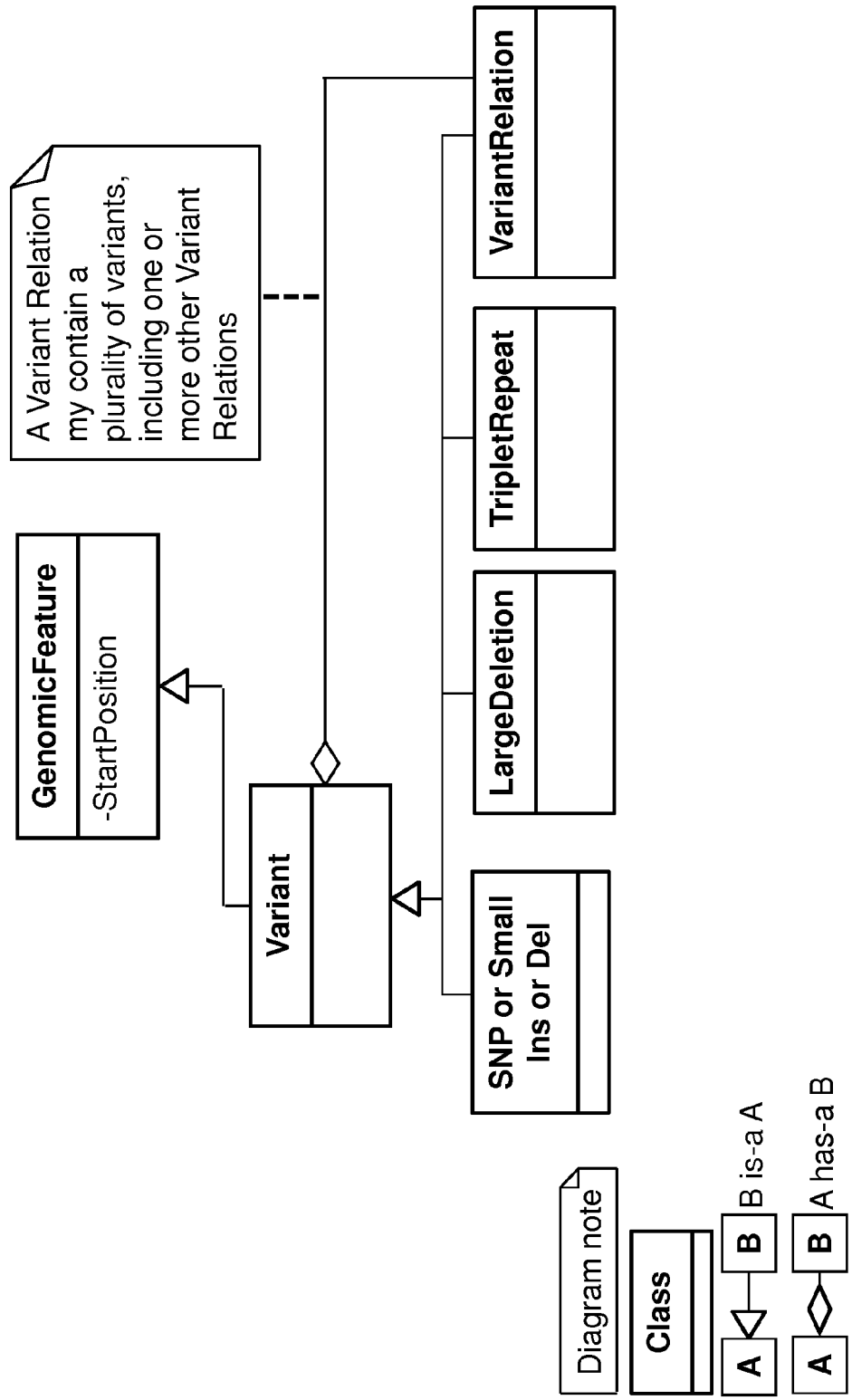
FIG. 2 is a diagram modeling a role of a variant relation according to some embodiments.

FIG. 2 shows the implementation of variant relation as a subtype of variant that can also contain variants. Since a variant relation can contain any number of variants, including other variant relations, it is possible to model very simple to very complex genomic relationships with a single, simple design. A variant relation object can be instantiated to capture information semantically significant to a particular type of relationship.

Accordingly, the invention provides systems and methods for the production of reports that include descriptions of genetic variants for a patient and information significant by virtue of relationships among variants therein. For example, a mutation may be found within a human mitochondrial genome (e.g., m.593T>C) that is not reported to have clinical statistical significance on its own. An SNP object can store this as a variant. Where the literature has reported that this variant with another variant (i.e., m.11778G>A) exhibits a synergistic effect on the severity of Leber's hereditary optic neuropathy (LHON), a variant relation object can be created containing the m.593T>C variant object and the m.11778G>A variant object, and the variant relation object can include the reporting information such as the results described in Zhang, et al., Is mitochondrial tRNAphe variant m.593T>C a synergistically pathogenic mutation in Chinese LHON families with m.11778G>A?, PLoS ONE 6(10): e26511 (2011).

As another illustrative example, people who have two mutated copies of the BRCA2 gene are reported to be susceptible to Fanconi anemia. While not all variants within the BRCA2 gene are detrimental, there are a number of different known variants that are known to be detrimental. Further, the BRCA2 protein requires the protein products of the CHK2 and FANCD2 genes, so mutations in those genes can—when present in combination with certain variants in the BRCA2 gene—be oncogenic (see, e.g., Yoshida, K., and Miki, Y., Role of BRCA1 and BRCA2 as regulators of DNA repair, transcription, and cell cycle in response to DNA damage, Cancer Sci 95(11):866-71 (2004); Friedenson, B., BRCA1 and BRCA2 pathways and the risk of cancers other than breast or ovarian, Med Gen Med 7(2):60 (2005).) Here, a number of variants are known and combinations of those variants are known, or suspected to be, either pathogenic or benign. Each known pathogenic combination can be represented by a variant relation that contains the relevant variants as well as supporting documentation from the literature.

Thus it can be seen that systems and methods of the invention can capture various types of associations among variants including, for example, variants in cis, recessive homozygous, complex combinations, and mitochondrial variants. Further associations that can be captured include heterozygosity (or loss of heterozygosity), for example, in somatic cells. In some embodiments, a variant relationship can be used to represent heterozygosity in non Mendelian frequencies such as, for example, 33%, 10%, 1%, or 0.01%.

Variant relation objects can be used to describe many combinations and associations of variant objects (which include other variant relation objects) thus providing a mechanism for systems and methods of the invention to tailor reporting to the real-world semantic relationship among genetic information.

Figure 3:
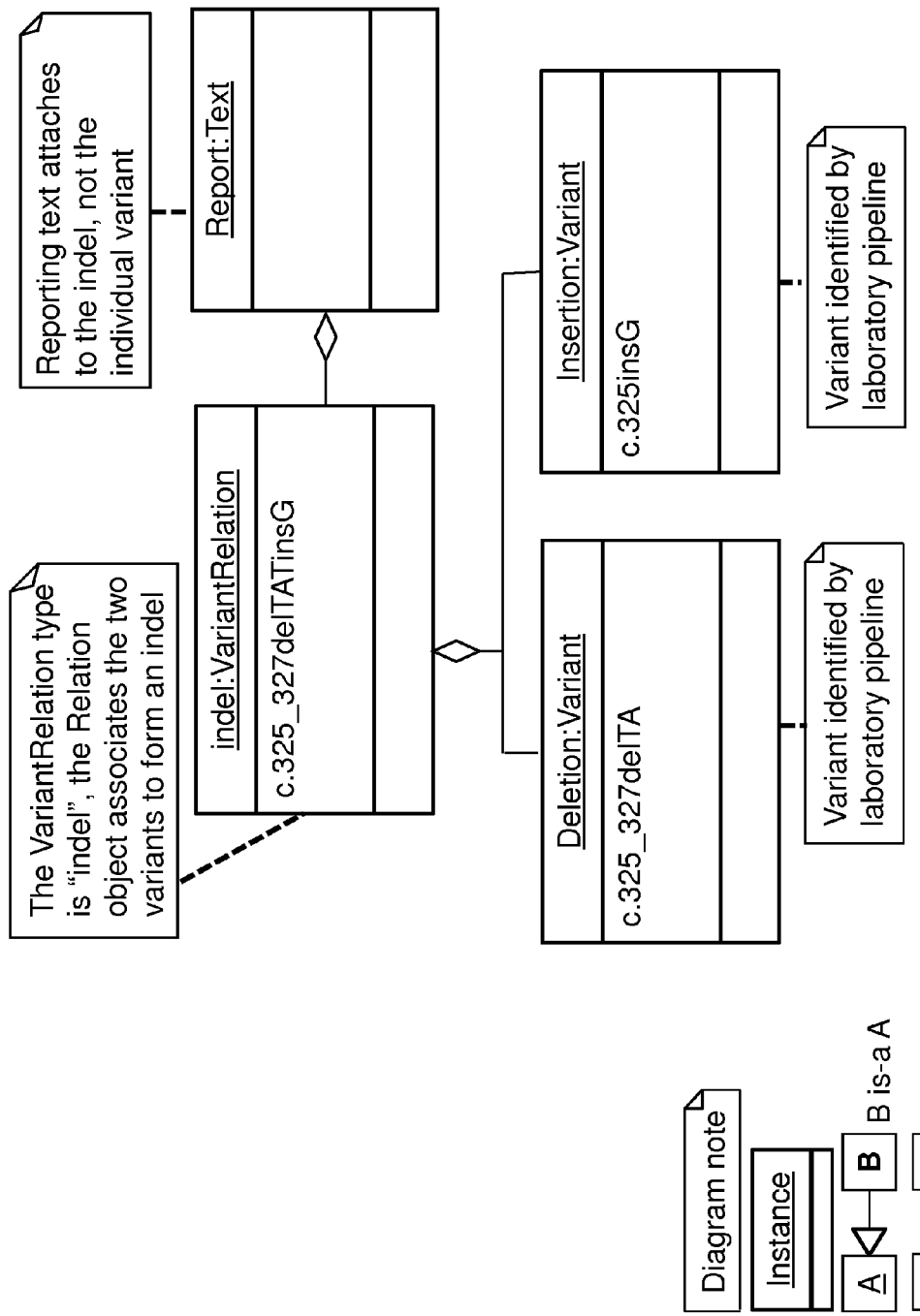
FIG. 3 is a diagram modeling use of a variant relation to capture an indel.

FIG. 3 shows the situation where the variant relation is used to capture an indel where the insertion and deletion are next to each other. In this example, systems and methods of the invention operate where next-generation sequencing (NGS) assay pipeline results identify a deletion variant (c.325_327delTA) as well as an insertion variant (c.325insG). In some instances, NGS analysis will not be able to characterize the deletion and the insertion together as an indel. For example, existing NGS read assembly algorithms have particular difficulty interpreting variants that should appear at or very near the ends of individual sequence reads. Here, those variants are captured as shown in FIG. 3, and a computer application is used to associate the two variant objects as an indel. Specifically, the computer application receives the results from, for example, the NGS assay pipeline. The application processes the NGS results and retrieves a deletion variant object named c.325_327delTA from a database and retrieves an insertion variant object named c.325insG from the database. The NGS results lead the application to compose (if the first instance) or retrieve from the database (if present) the appropriate variant relation object c.325_327delTATinsG. This variant relation references a deletion variant named c.325_327delTA and an insertion variant named c.325insG. The variant relation has report text for the patient report attached. This reporting text will refer to the indel captured by the variant relation. Thus, the variant relation allows the reporting text to be connected at the correct semantic level.

It is noted here that FIG. 3 is an "instance level diagram", sometimes called an "object diagram", representing instances of genetic information as stored in, or reported by, systems and methods of the invention. In comparison, FIG. 1 generally represents use of a "class diagram". As can be seen from these figures, unified modeling language (UML) is useful for diagramming aspects of embodiments of the invention. Diagrams in UML such as class diagrams and instance-level diagrams are discussed in Roff, UML: A Beginner's Guide, McGraw-Hill, Berkeley, Calif. 314 pages (2003).

Figure 4:
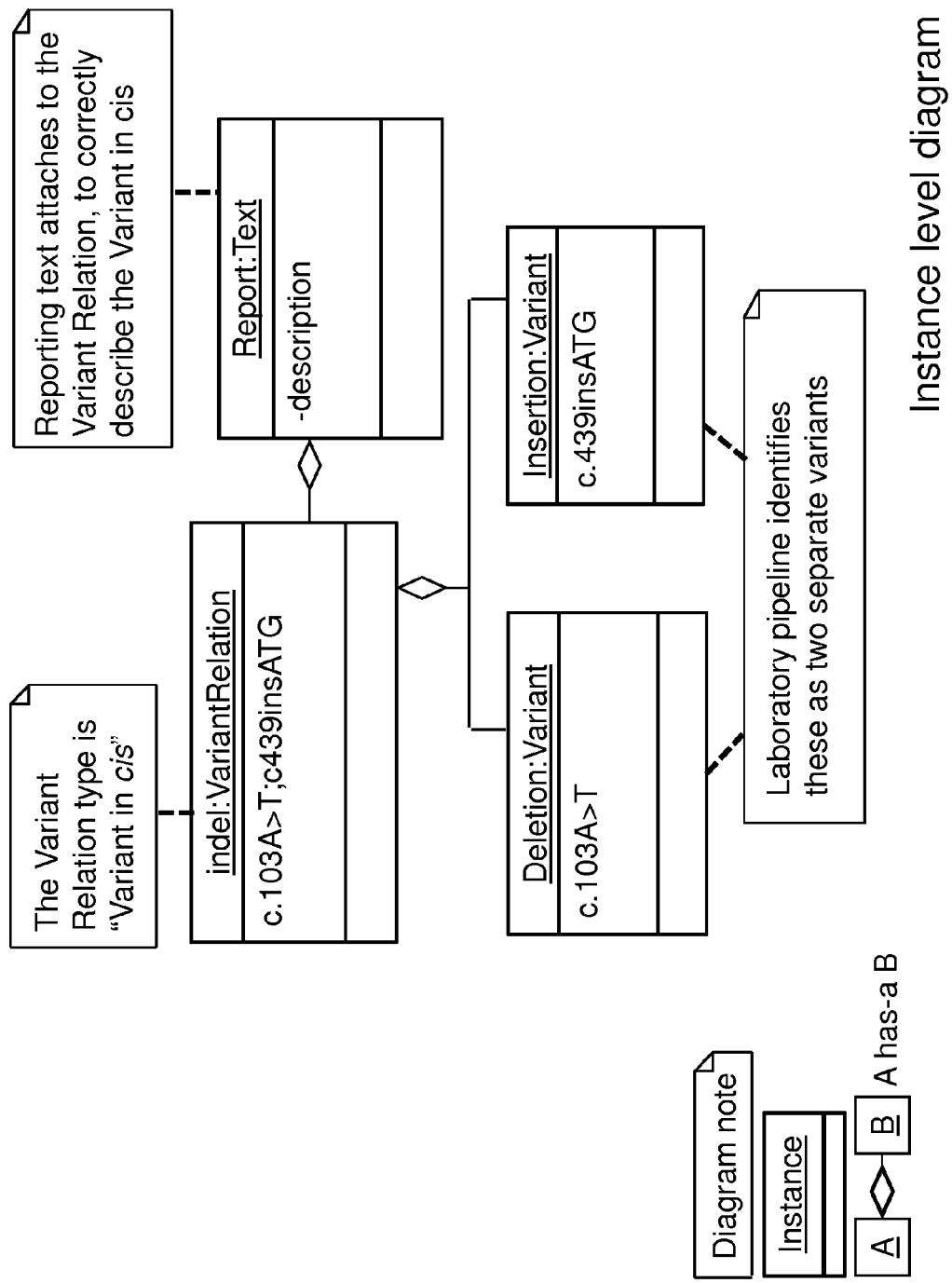
FIG. 4 is a diagram modeling use of a variant relation to capture a variant in cis.

FIG. 4 is a diagram modeling use of a variant relation to capture a variant in cis. Here, two variants could be identified by unlike assay pipelines (e.g., MLPA and genotyping, or MLPA and HiSeq). In the report production environment, the application processes one set of assay pipeline results and retrieves a variant object named c.103A>T from the database and processes another set of results to retrieve the c.439insATG variant object. The application calls a variant relation object showing these as variants in cis and produces a report based on reporting text attached to the variant relation. It should also be noted, as will be discussed in greater detail below, that similar underlying concepts apply in the database development environment. In development, information about the c.103A>T variant is received into the system (e.g., from assay pipeline results, manually keyed in, imported from literature or legacy systems, etc.) and an instance of a variant object is instantiated. The instance is given a value for its name attribute, which can be, for example, a string data type attribute. In the embodiment illustrated in FIG. 4, the name attribute string is given a value of c.103A>T, and the newly instantiated object is stored in the database. In like fashion, a c.439insATG object is instantiated and stored in the database. The c.103A>T;c439insATG variant relation object can also be instantiated and stored in the database and any reporting text can be provided for each object. This data will then be available when the database from the development environment is made available to the production environment.

A variant database according to the invention can be used to report complex genetic relationships in a nimble, dynamic fashion. New information can be introduced by instantiating new objects without disrupting the existing structure or data. It will be appreciated that a number of genetic variants can produce many combinations For example, where a bi-allelic (A or B) diploid locus and a tri-allelic (C, D, or E) diploid locus are proximal to one another in, for example, a gene, an individual may have any of six genotypes (AC, AD, AE, BC, BD, or BE) on either chromosome for a total of 21 diploid genotypes. However, a number of variant types, such as polynucleotide repeats and copy number variants, can have numerous alleles. Further, the number of variants associated with clinical significance, be they SNPs, indels, polyN variants, etc., is large and ever-growing. The invention allows for agile reporting of the known clinical significance of combinations of the variants.

Figure 5:
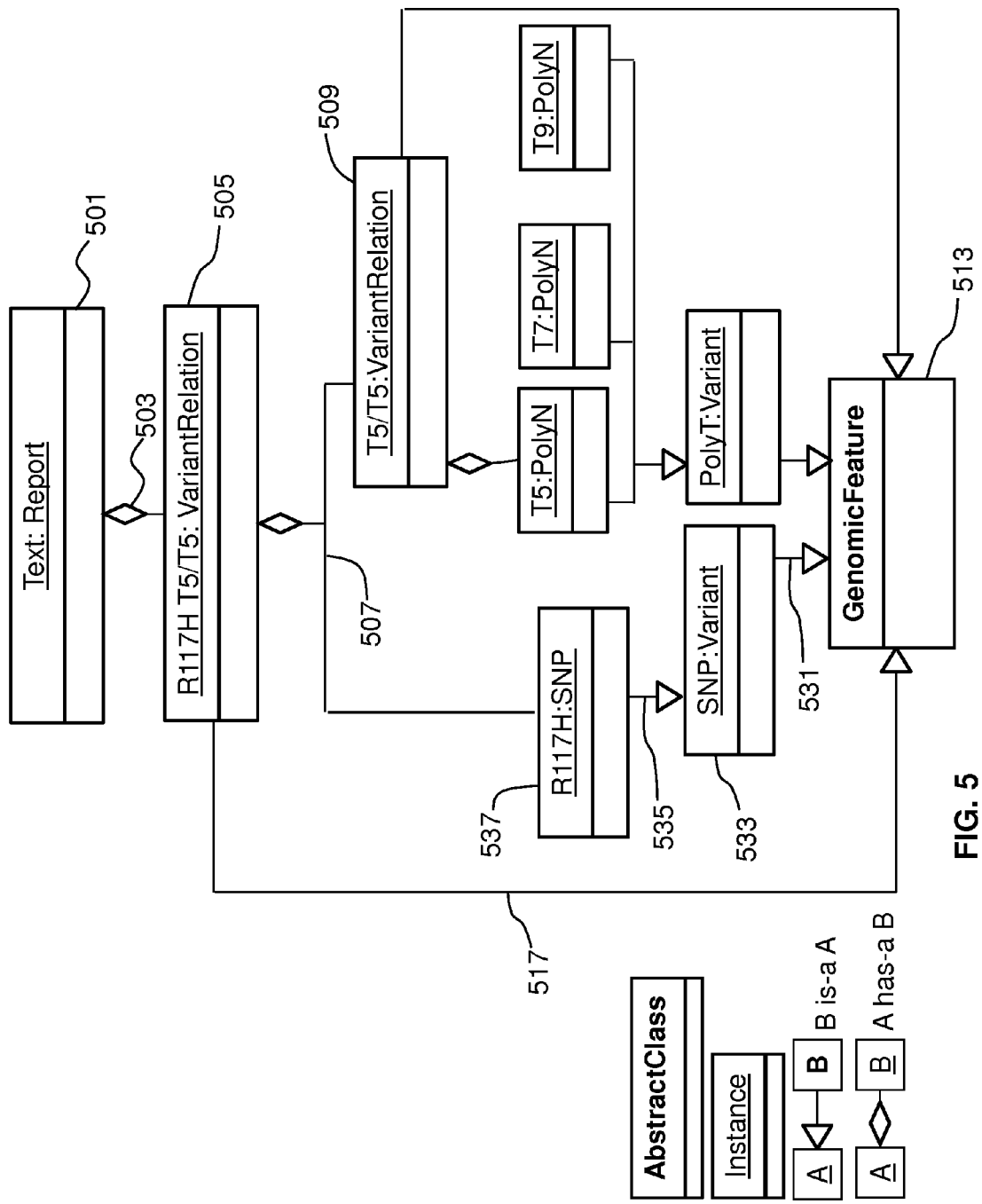
FIG. 5 is a diagram modeling inheritance and composition according to embodiments.

FIG. 5 is a diagram modeling inheritance and composition according to embodiments. FIG. 5 uses variants associated with cystic fibrosis to illustrate the operation of systems and methods of the invention. While FIG. 5 uses variants associated with cystic fibrosis, the principles illustrated therein are of general applicability.

Cystic fibrosis is a genetic disease affecting the lungs caused by mutations in the cystic fibrosis transmembrane conductance receptor (CFTR) gene located on the long arm of chromosome 7. Over 1,500 mutations, or variants, of the gene are known. One class of mutations includes R117H (i.e., c.350G>A based on GenBank cDNA reference sequence NM_000492.3) and interferes with normal ion transport. The phenotypic consequences of R117H may be attributable to the presence of a poly-T variant in the acceptor splice site of intron 8 of CFTR in cis with R117H. Common variants of this poly-T site are T5, T7, and T9 and evidence supports the role of T5 in pathogenic alternate splicing or exon skipping. Aspects of the genetics of cystic fibrosis are discussed in Rowntree and Harris, The phenotypic consequences of CFTR mutations, Ann Hum Gen 67:471-485 (2003); Thauvin-Robinet, et al., The very low penetrance of cystic fibrosis for the R117H mutation: a reappraisal for genetic counseling and newborn screening, J Med Genet 46:752-758 (2009); and Kreindler, Cystic fibrosis: exploiting its genetic basis in the hunt for new therapies, Pharmacol Ther 125(2):219-229 (2010), the contents of each of which are hereby incorporated by reference in their entirety.

The relation among the R117H variant, the T5 variant, the T7 variant, and the T9 variant can be illustrated using the concepts illustrated by the diagram shown in FIG. 5. As seen in FIG. 5, each variant and variant relation is an instance of the abstract class of genomic feature 513.

For example, since R117H represents as a single nucleotide polymorphism in which an adenine is substituted for a guanine at the position represented by nucleotide 350 of the cDNA sequence represented in GenBank by reference number NM_000492.3, systems and methods of the invention create a variant object 537 that has an "is-a" relationship 535 with an SNP:Variant class 533 that itself has an "is-a" relationship 531 with the abstract class 513. That is, variant 537 is an instance of class 513. Similarly, a variant object is created for the T5 variant as an instance of a class of PolyT: Variant that is a subclass of abstract class 513. Objects are also created for the T7 and T9 variants. Where a result indicates that a patient has a genotype that is homozygous for T5, a T5/T5 variant relation 509 is created. Further, systems and methods of the invention can create a R117H T5/T5 variant relation object 505 that contains 507 the variant object 537 and the T5/T5 variant relation 509. Note that variant relation object 505 also is 517 itself an instance of the abstract class of genomic feature 513. Systems and methods of the invention can thus be used to produce a report 501 that contains 503 the R117H T5/T5 variant relation object 505 and thus provides a description of genetic variants for a patient.

It should further be appreciated that the label R117H refers to an amino acid substitution. Here, if either the amino acid substitution or the nucleotide variant (e.g., c.350G>A) is included, object 537 can still be instantiated and, further, relation 505 could use either an amino acid variant object or a corresponding nucleotide variant object. In certain embodiments, a computer application interprets the amino acid string to instantiate a nucleotide variant object.

Using the object hierarchy as discussed above, assay pipeline data is used to create a genotypic model in a production environment. A variant in the data is identified (e.g., by comparison to a reference such as hg18) and a variant object is invoked. As needed, other variant objects are invoked, each containing the data from the assay pipeline. Based on the assay pipeline to reference comparison, the relationships among the variants are invoked as relation objects from the database and the associated text or content is provided in a report.

Systems and methods of the invention provide for numerous such transactions with rapid turn-around times by using and re-using the objects provided by a database. Using techniques associated with online transaction processing, systems and methods of the invention can rapidly provide reports based on incoming assay pipeline data requiring a complex array of relationships among the underlying variants.

Figure 6A:
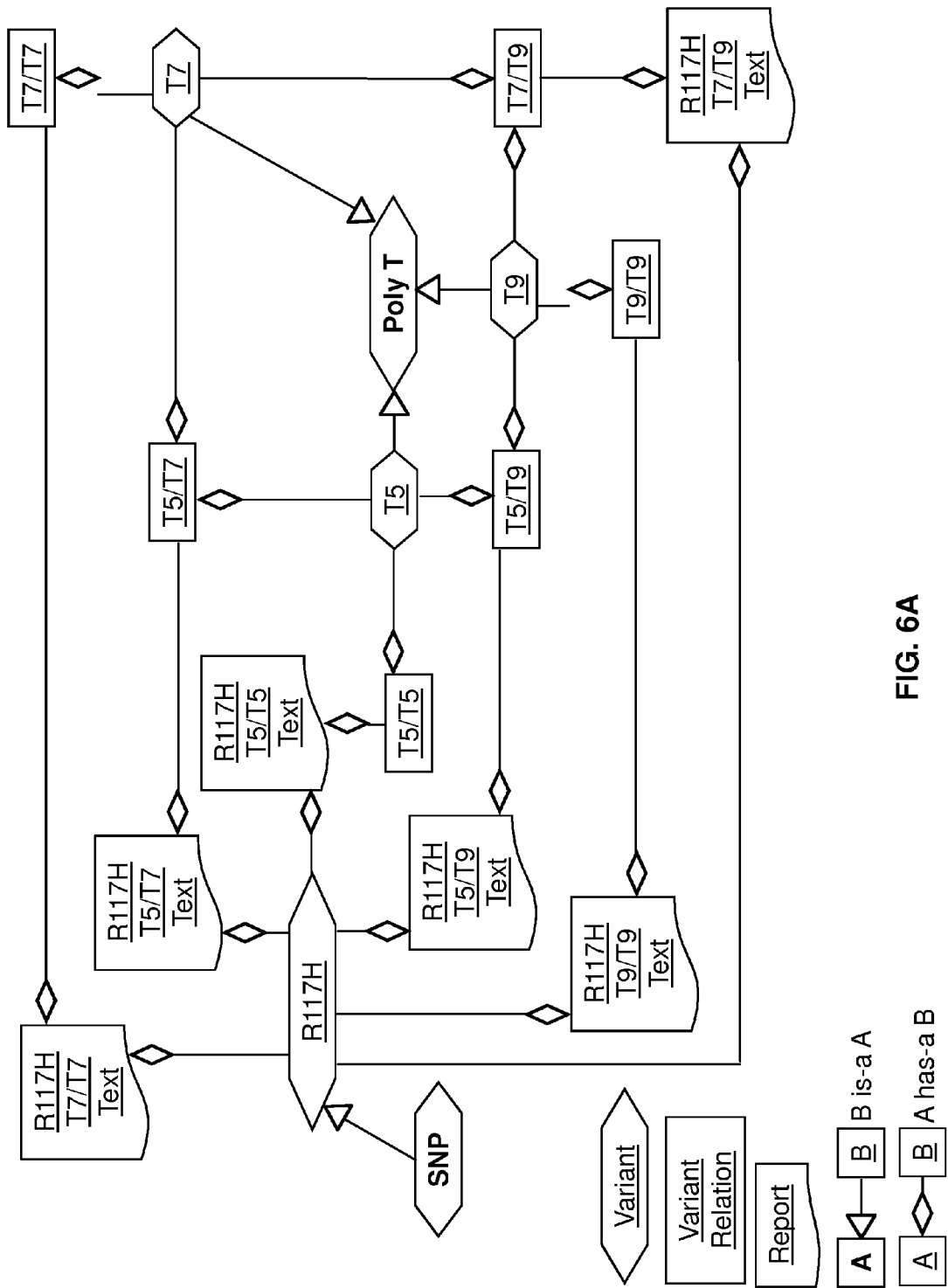
FIG. 6A shows use of the invention to provide variant descriptions.
Figure 6B:
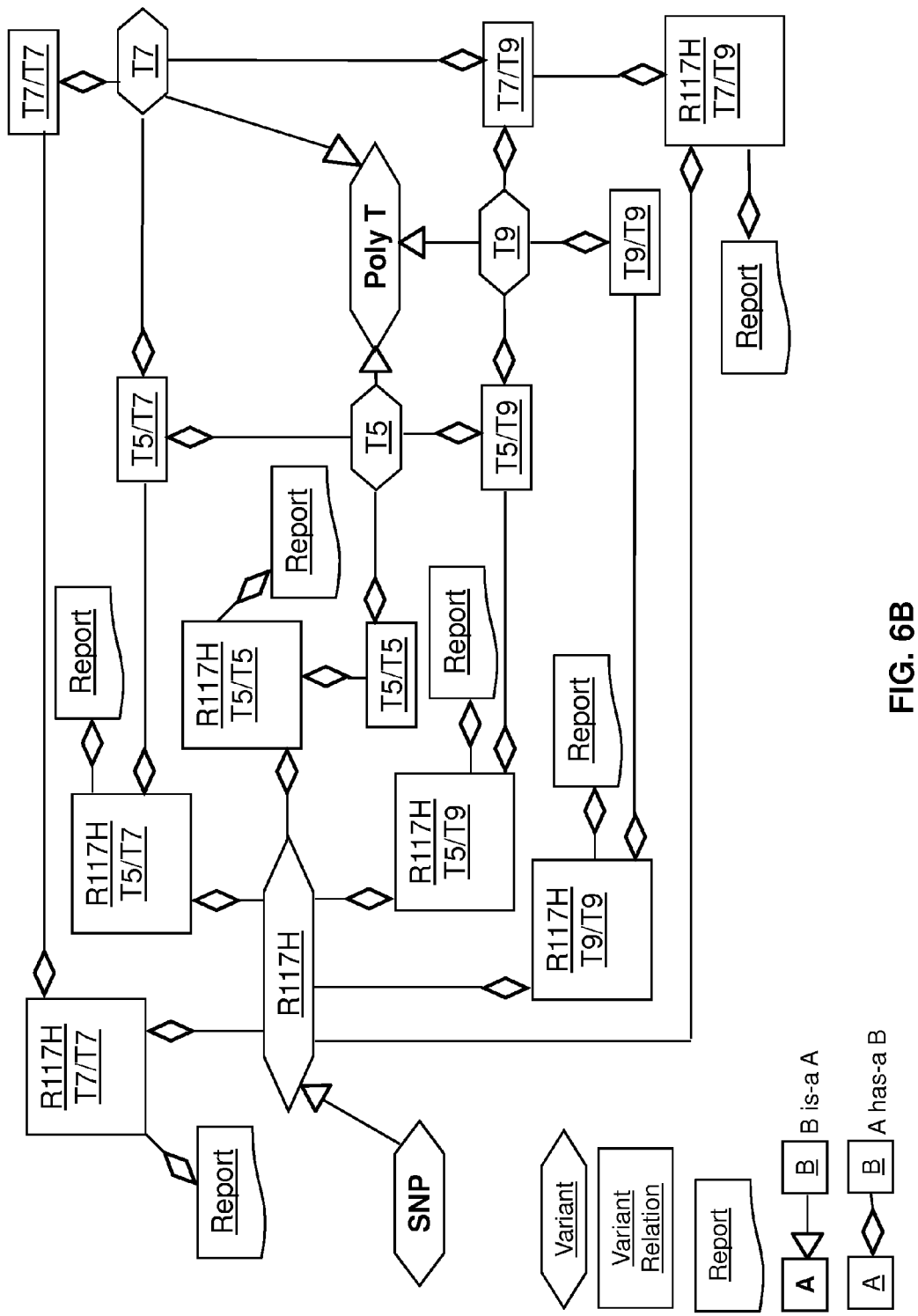
FIG. 6B shows an alternative embodiment of the use illustrated in FIG. 6A.

FIGS. 6A and 6B show use of the invention to report multiple complex relationships among R117H and polyT variants. This particular in cis relationship was selected because it is both relatively frequent and very complex to represent. As discussed above, in cystic fibrosis, the R117H variant must be examined in tandem with another variant, called polyT. Whether or not the combination is pathogenic may depend on the number or nature of polyT repeats. The combinations that must be represented are shown in FIG. 6A in the report boxes (which, in this embodiment, are themselves instances of the abstract class of genomic feature). FIG. 6B shows an alternative embodiment, in which the report contains the variant relationship. Either embodiment and related effective embodiments are within the scope of the invention.

Making reference to FIG. 6B, it will be seen that both R117H and polyT are represented by corresponding variant objects. Since polyT is, in fact, a class of variants, it is represented by a super class (bold type, no underlining) that is a subclass of the abstract superclass of genomic feature (not shown in FIG. 6B). Since R117H is a specific variant, it is represented by an object shown to be an instance (underlined type) of a class. The polyT super class is, in turn, instantiated as T5, T7, and T9. Each diploid combination of the T5, T7, and T9 object is shown as a variant relation object that is itself an instance of the abstract superclass of genomic feature. Each diploid combination of polyT variant is, in turn, shown in combination with the R117H variant, as a variant relation (e.g., the blocks labeled R117H T7/T7, R117H T5/T7, etc.).

Systems and methods of the invention are provided to handle relations among variants much more complex than those represented in FIG. 6A or 6B. In certain embodiments, systems and methods of the invention can provide descriptions of variants and accommodate all reported variants and combinations and provide distinct reporting text with each. For example, once the R117H/polyT structure is correctly represented, the annotations associated with the variant relations can be expanded, and new variants and new variant relations can be added, without any limitation imposed by the design.

Thus, with the addition of T6, for example, existing files, queries, sort orders, or look-up keys need not be modified. See, for example, Huang, et al., Comparative analysis of common CFTR polymorphisms poly-T, TG-repeats and M470V in a healthy Chinese population, World J Gastroenterol 14(12):1925-30 (2008). If an assay pipeline gave results indicating a R117H T6/T9 variant, with T6 not yet represented, applications of the invention can be operated to invoke and create a new variant object, inheriting attributes and methods from the abstract class of genomic feature. Then, R117H is fetched and T9 is fetched; a T6/T9 relationship is instantiated and made to contain the new T6 variant and the existing T9 variant. The T6/T9 relation object and the R117H object are related by a relation object that is then created. In certain embodiment, a physician in the production environment can then cause the new objects to be contributed to the database, either directly or by transmitting the new objects to the development environment where they are further curated by geneticists. The physician or geneticists may further contribute clinically significant information, for example, to either the T6 variant object, the new R117H T6/T9 relation object, or both (referencing, for example, Huang 2008). Based on objects in the database, or newly created objects as-needed, the application provides a description of genetic variants for a patient by producing a report containing material associated with the appropriate variant relation or variant objects.

Further, implementations of systems of the invention are extensible using, for example, multiple parallel processors or storage virtualization devices such as redundant arrays of independent disks (RAID memory), as discussed in more detail below. Accordingly, systems and methods of the invention can support a high number of contemporaneous users and transactions.

In some embodiments, implementations of the invention benefit from high throughput use by exploiting high volumes of transactions to support the growth of the underlying substantive contents of the database. For example, every novel variant or relation can be tagged—given appropriate anonymization and informed consent. Thus input of a new variant and associated information via the curation of incoming results makes that new variant, associated information, and containing relationships available. In some embodiments, new variants are made available substantially immediately (e.g., data is anonymized and released into production). Moreover, where the subject genetic information relates to an infectious agent and not to genetic information of a patient (e.g., the genetic information concerning variants of anthrax or West Nile virus), there may be clinically significant genetic information that does not required patient consent or other regulatory compliance for shared use, and embodiments of the invention may provide rapid, global bio-threat response tools. Further, embodiments of the invention may be implemented in a distributed pattern, with system users working in different buildings or even cities to curate results or generate reports as ordered by medical professionals.

As discussed herein, embodiments of the invention are disclosed suitable for deployment in a clinical environment. In some embodiments, systems and methods of the invention receive assay pipeline results from laboratories via laboratory information management systems (LIMS) and use a production terminal to present a dashboard interface engine for use by a system user to review and finalize reports.

Figure 7:
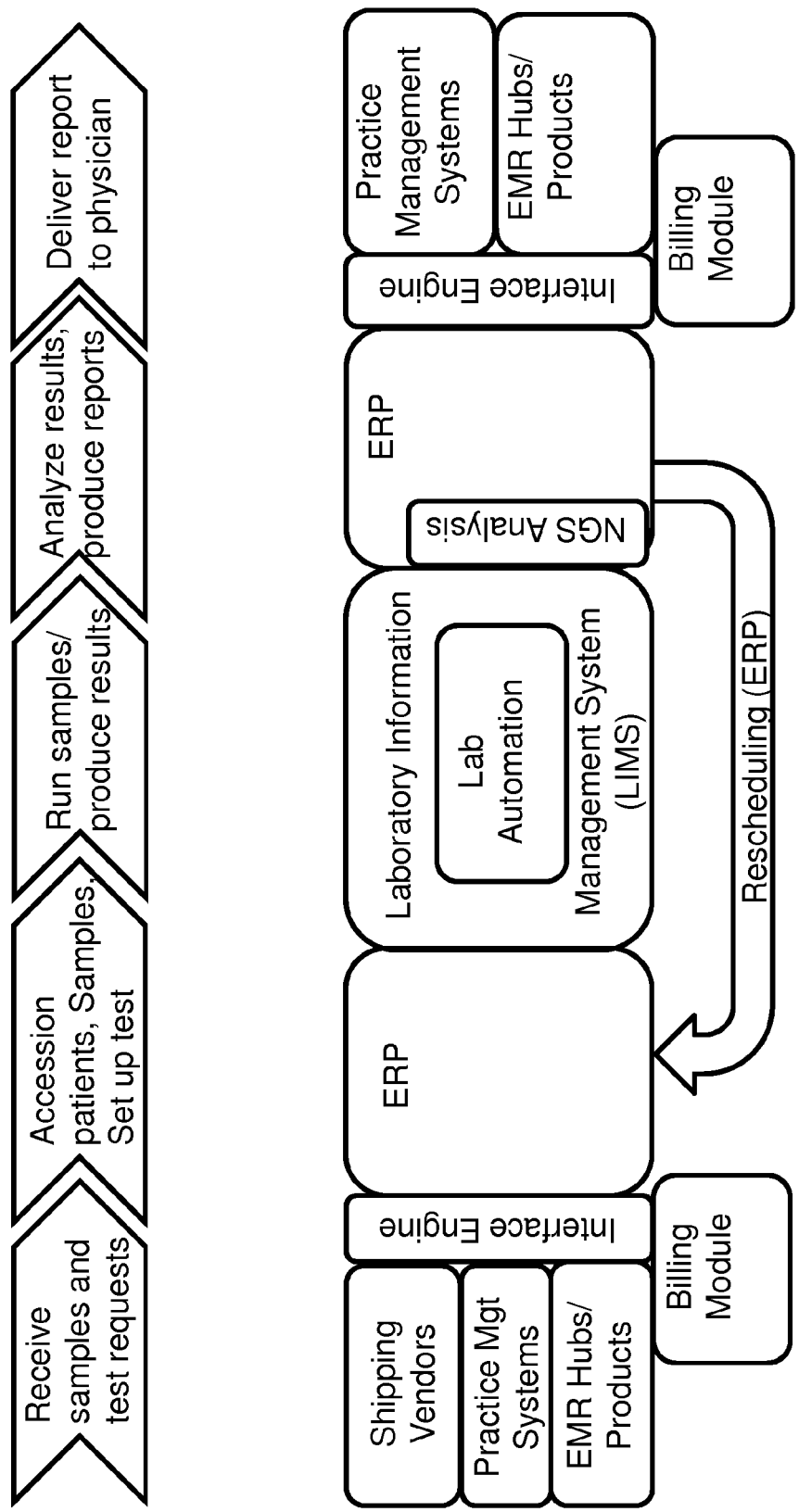
FIG. 7 is a diagram of a workflow making use of the invention.

FIG. 7 is a diagram of a workflow according to certain embodiments of the invention relating to production environments. Components illustrated in FIG. 7 show exemplary aspects of one clinical environment within which embodiments of the invention may be employed. FIG. 7 depicts shipping, vendor, practice management, billing, and electronic medial record (EMR) systems that feed into a clinical Enterprise Resource Planning (ERP) system. Systems external to the ERP system such as the EMR or billing system can interface via standard HL7 messaging. From the left side of FIG. 7, ERP handles all internal sample accessioning and test order processing. On the right side, ERP handles the management of the results that return from potentially many assay pipelines. The results can be brought together in a user interface 'dashboard' that enables a laboratory director to assign reporting categories. At patient report generation time, the reporting category triggers the rules that pick up the correct report text to add to the appropriate test result in the report.

A LIMS (Laboratory Information Management System) is shown in FIG. 7, with a laboratory automation module internal to it. Lab automation provides for the set up and running of liquid handling robots. Sample chain-of-custody is assured through the entire workflow.

Due to the assay pipeline integration, the disclosed system accommodates both automatically derived and manually entered results over a wide range of assays. For example, the system automatically analyzes NGS results (e.g., from the Illumina HiSeq DNA sequencer) using an NGS assay pipeline shown in FIG. 7. Other assay pipelines provide results that can be entered by the scientist or laboratory technologist specializing in that particular assay (e.g., MLPA, genotyping, and so forth). The system itself can extend to accommodate a wide range of different types of assays.

Figure 8:
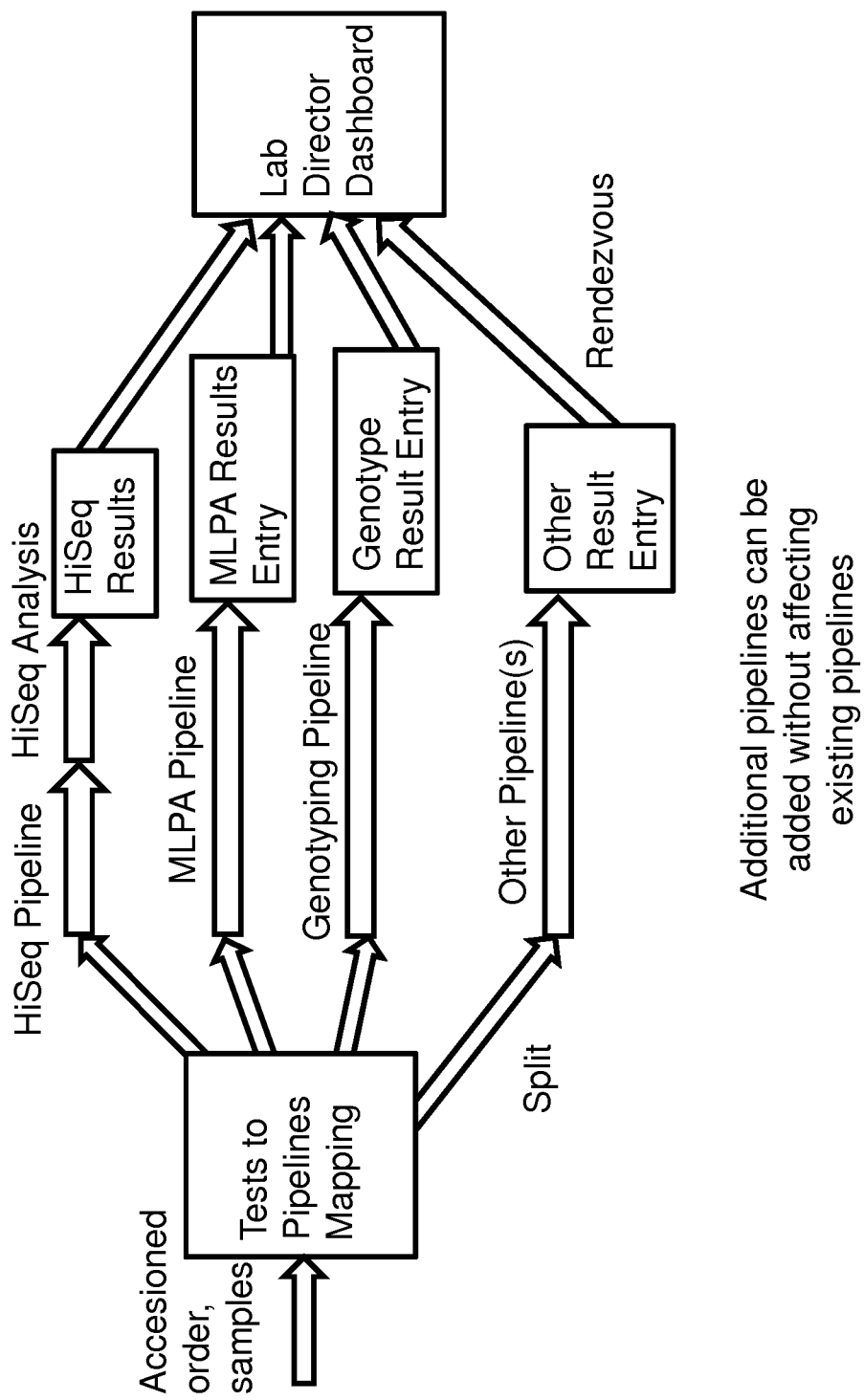
FIG. 8 shows workflow use of split and rendezvous to integrate assay pipelines.

FIG. 8 gives a view of the ERP and LIMS processing according to a classic workflow split/rendezvous model. A given test requisition may order cystic fibrosis, alpha thalassemia, and fragile X tests. When translated into assay pipelines (the "split"), these particular tests will result in many different assay pipelines. Those particular tests, for example, will result in DNA extraction, DNA quantitation, NGS sequencing, MLPA, genotyping, and triplet-PCR primary assay pipelines, plus potentially methylation, Sanger sequencing, and genotyping confirmatory assay pipelines. In addition, any number of assay pipelines may be repeated for redo purposes. The presence of, identity of, and number of assay pipelines depicted in FIG. 8 is purposefully open ended, as represented by "Other Pipeline(s)." Other possible assay pipelines potentially include any discussed herein, as well as other laboratory and scientific assay pipelines known in the art, and further including manual entry of information and digital or electronic capture of information such as retrieval of variant information from online databases and other sources in bulk or case-by-case, done manually or automatically. In some embodiments, genetic data relating to a patient is received via a sequencing assay pipeline (e.g., an NGS technology such as HiSeq) and analyzed to determine that the data represent one or more mutations, e.g., as variants respective to a reference.

In some embodiments, variants are picked up from the variant database for the NGS assay pipeline processing shown in the top assay pipeline in FIG. 8. The fast lookup afforded by the variant data design according to the invention enables rapid turn-around time (TAT) for production of a patient report. Rapid turn-around time through fast report generation provides an accurate and valuable clinical diagnostic product.

Each result module depicted on the right side of FIG. 8 can use a look up in the variant database to provide a result report into the dashboard, or interface engine. Results may be looked up and reported automatically or with human intervention, depending on the nature of the assay or the implementation of the embodiment. The overall system architecture continues the extensibility principle of the disclosed variant database design. New assay pipelines may be added to the system without disrupting existing assay pipelines, just as new variants/mutations may be added to the variant database without disrupting existing variants already used in patient reporting. Existing assay pipelines can be obsolesced, for example, as genes covered by the older assays are subsumed into NGS or other assay pipeline processing.

As results are processed, the variant database data representation drives the user interface and results amalgamation for generation of a patient report. The patient report may be generated by a report generation module, which can be triggered by a laboratory director's approval event from the lab director dashboard. In some embodiments, the system automates one or more reporting category selection, e.g., for deterministic situations where a negative result is indisputable. In certain embodiments, in some cases, the system assists the laboratory director in making an informed choice on patient results. Further, systems and methods of the invention combine results as needed from assay pipelines and generate a composite report, which can then be inspected or approved by a laboratory director or physician. Report generation uses the variant data to report the variant seen on the patient report. Moreover, the variant data model of the invention enables identification of the variant irrespective of the type of assay used for the experiment.

Figure 9:
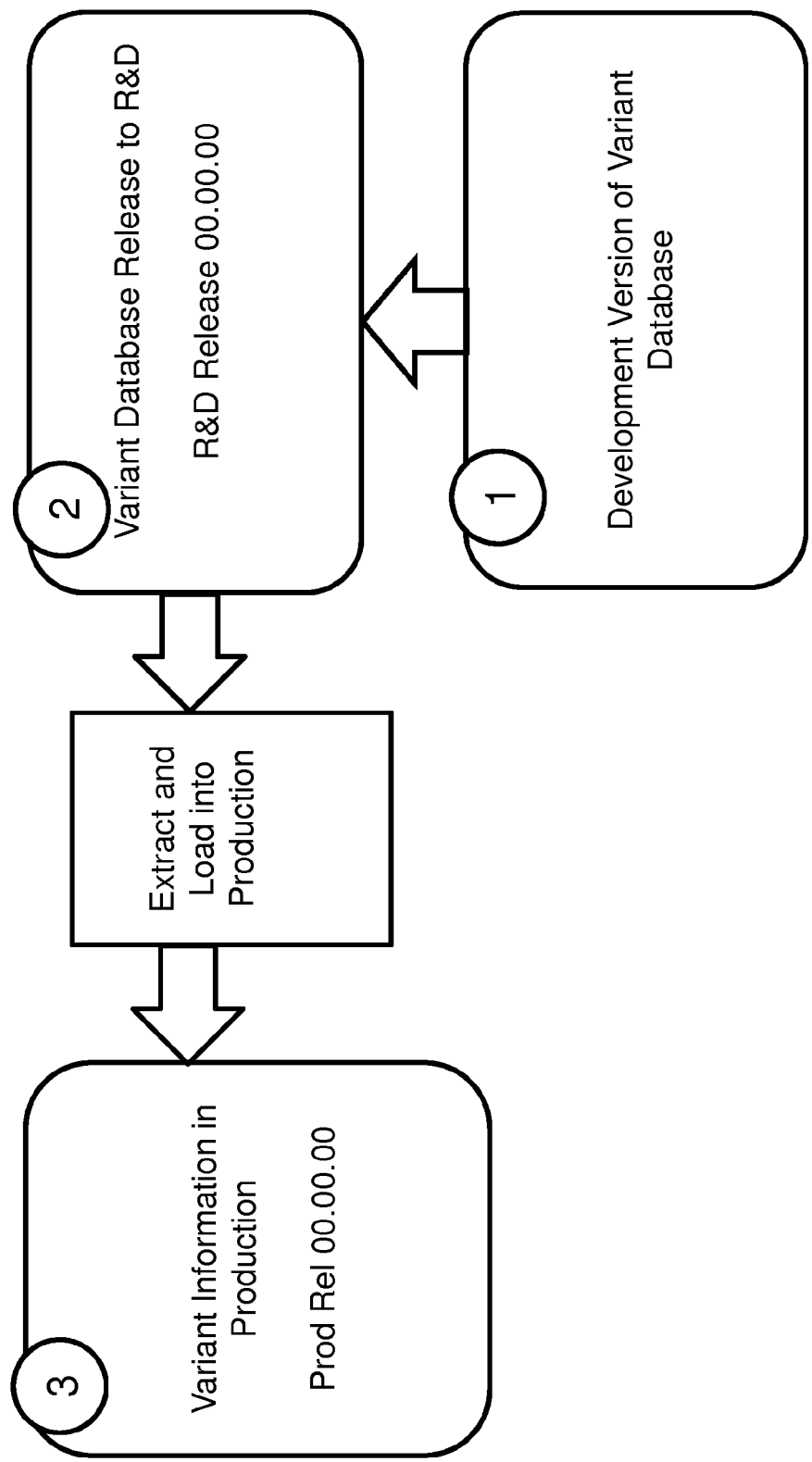
FIG. 9 gives a high-level diagram of development, research, and production embodiments.

FIG. 9 gives a high-level diagram of development, research, and production embodiments. At step 1, a database system is developed and genetic data is curated for inclusion in the development database. Development of the underlying database system can include creation or programming of the object-oriented code and structures to implement embodiments of the invention, for example, as shown in FIGS. 1-6.

Figure 10:
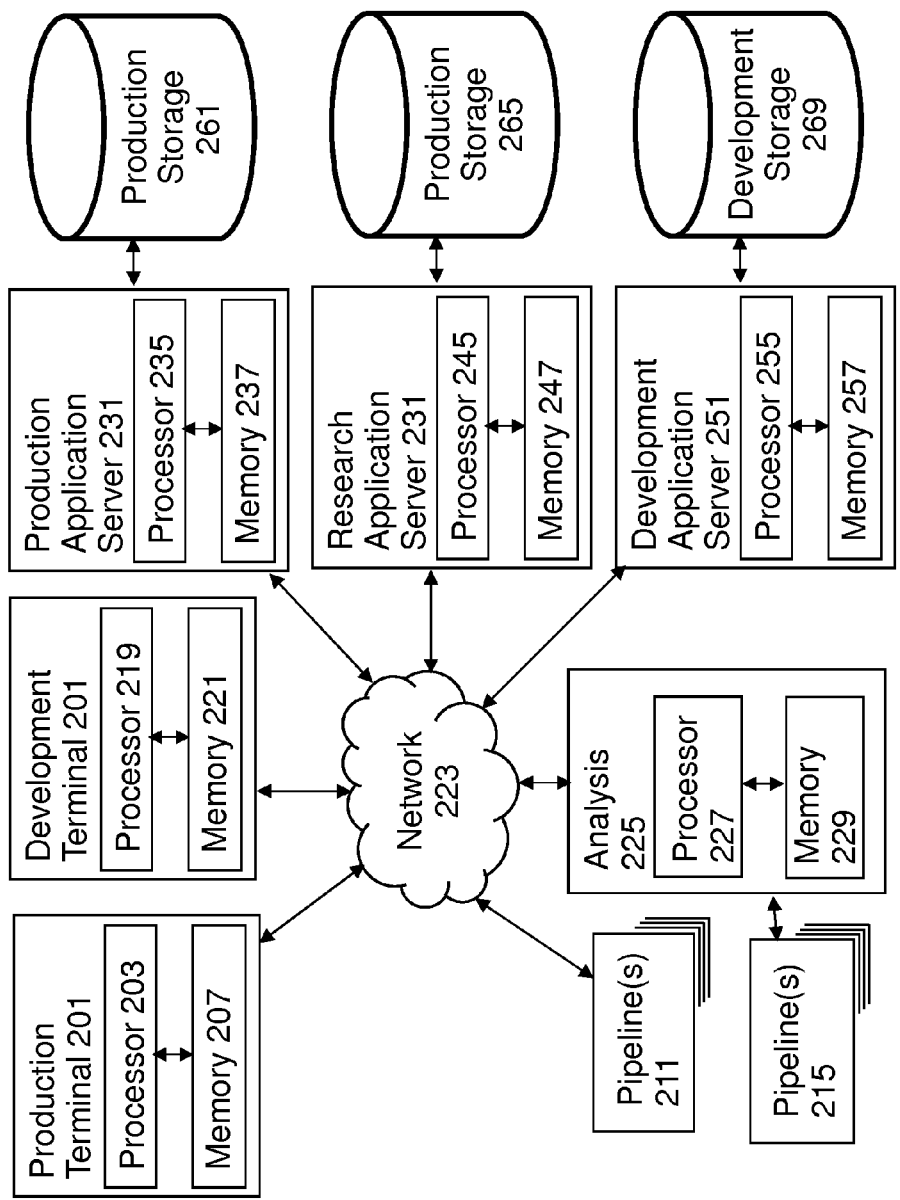
FIG. 10 diagrams a system for providing or describing variants according to certain embodiments.

FIG. 10 diagrams a system for providing or describing variants according to certain embodiments. A database application can be developed for use on a development application server 251 that includes processor 255 and memory 257. The database can be housed in development storage 269. Any development environment, database, or language known in the art may be used to implement embodiments of the invention. Preferably, an object-oriented development language, database structure, or development environment is used. Exemplary languages, systems, and development environments include Perl, C++, Python, Ruby on Rails, JAVA, Groovy, Grails, Visual Basic .NET. In some embodiments, implementations of the invention provide one or more object-oriented application (e.g., development application, production application, etc.) and underlying databases for use with the applications. An overview of resources useful in the invention is presented in Barnes (Ed.), Bioinformatics for Geneticists: A Bioinformatics Primer for the Analysis of Genetic Data, Wiley, Chichester, West Sussex, England (2007) and Dudley and Butte, A quick guide for developing effective bioinformatics programming skills, PLoS Comput Biol 5(12):e1000589 (2009).

In some embodiments, a database application is developed in Perl (e.g., optionally using BioPerl). Object-oriented development in Perl is discussed in Tisdall, Mastering Perl for Bioinformatics, O'Reilly & Associates, Inc., Sebastopol, Calif. 2003. In some embodiments, a database application, database, and production application are developed using BioPerl, a collection of Perl modules that allows for object-oriented development of bioinformatics applications. BioPerl is available for download from the website of the Comprehensive Perl Archive Network (CPAN). See also Dwyer, Genomic Perl, Cambridge University Press (2003) and Zak, CGI/Perl, 1st Edition, Thomson Learning (2002).

In certain embodiments, applications and databases are developed using Java and optionally the BioJava collection of objects, developed at EBI/Sanger in 1998 by Matthew Pocock and Thomas Down. BioJava provides an application programming interface (API) and is discussed in Holland, et al., BioJava: an open-source framework for bioinformatics, Bioinformatics 24(18):2096-2097 (2008). Programming in Java is discussed in Liang, Introduction to Java Programming, Comprehensive (8th Edition), Prentice Hall, Upper Saddle River, N.J. (2011) and in Poo, et al., Object-Oriented Programming and Java, Springer Singapore, Singapore, 322 p. (2008).

Applications and databases of the invention can be developed using the Ruby programming language and optionally BioRuby, Ruby on Rails, or a combination thereof. Ruby or BioRuby can be implemented in Linux, Mac OS X, and Windows as well as, with JRuby, on the Java Virtual Machine, and supports object oriented development. See Metz, Practical Object-Oriented Design in Ruby: An Agile Primer, Addison-Wesley (2012) and Goto, et al., BioRuby: bioinformatics software for the Ruby programming language, Bioinformatics 26(20):2617-2619 (2010).

Systems and methods of the invention can be developed using the Groovy programming language and the web development framework Grails. Grails is an open source model-view-controller (MVC) web framework and development platform that provides domain classes that carry application data for display by the view. Grails domain classes can generate the underlying database schema. Grails provides a development platform for applications including web applications, as well as a database and an object relational mapping framework called Grails Object Relational Mapping (GORM). The GORM can map objects to relational databases and represent relationships between those objects. GORM relies on the Hibernate object-relational persistence framework to map complex domain classes to relational database tables. Grails further includes the Jetty web container and server and a web page layout framework (SiteMesh) to create web components. Groovy and Grails are discussed in Judd, et al., Beginning Groovy and Grails, Apress, Berkeley, Calif., 414 p. (2008); Brown, The Definitive Guide to Grails, Apress, Berkeley, Calif., 618 p. (2009).

One skilled in the art will recognize that different aspects or components of the invention may be developed or implemented using any of, or a combination of, development languages and environments such as those discussed herein. A development application can be developed using object-oriented techniques to describe variants based on entries in a development database with an object-oriented design and corresponding relational database schema.

In certain embodiments, the implementation of the development database uses the object-oriented (OO) principles of abstraction, inheritance, polymorphism, and containment, as discussed above. The development database (e.g., stored in development storage 269) thus provides an abstract class of genomic feature object. Development application 251 can be used to create variant objects, each being an instance of the abstract class of genomic feature object and comprising a description of a mutation. The data can be received via network 223 from, for example, assay pipelines 211, assay pipelines 215 and analysis system 225, production application 231, or research application server 241. Development geneticists or other personnel can input information about variants as data using development terminal 217 having memory 221 coupled to processor 219.

FIG. 10 shows a relationship among these components according to certain embodiments. Assay pipelines 215 may operate in integration with analysis system 225 having processor 227 coupled to memory 229. A production terminal 201 with memory 203 coupled to processor 207 can provide the dashboard (FIG. 8) of the interface engine (FIG. 7). Systems and methods of the invention are thus used to create relation objects, e.g., using development application 251, each relation object being an instance of the genomic feature object and comprising one or more genomic feature objects and a description of a relationship among the one or more genomic feature objects. All objects can be stored in a development version of a database (FIG. 9) in development storage 269 (FIG. 10). The development version of the database, or any research or production versions released therefrom, can be used to provide variant descriptions based on one of, or any number of, of the relation objects.

As shown in FIG. 9, a development version of the database is implemented in step 1. Step 2 represents an optional release of a research version. In some embodiments, patient data collected, for example, in the production environment, is anonymized and de-identified (subject to informed consent, compliance with regulations, etc.), and analyzed within the research database in R&D systems (e.g., as stored in research storage 265 in FIG. 10).

Novel variants of any characterization, e.g., pathogenic, suspected pathogenic, benign, etc. can be automatically added to the variant database as a new variant by the assay pipeline. Variants added in the production environment can be labeled or identified according to the clinic, lab, or enterprise providing the information. Existing or novel variants and relation objects can be tracked further using production information relation to frequency (i.e., number of times observed in individuals, possibly by ethnicity). Over time, genetic researchers or other parties can vet new data for potential inclusion into subsequent development versions and thus into the production instance of the database (step 3 in FIG. 9). Further, the database is versionable and each patient report that is produced can reference the version of the variant database used.

Turning back to FIG. 10, release from development can optionally provide a research database housed in research storage 265, for use via research application server 241 having processor 245 and memory 247. A production version of the database can be released and stored in production storage 261, to be accessed by production application server 231 having memory 237 coupled to processor 235.

While the storage, terminals, analytical systems, and servers are shown in FIG. 10 as discrete blocks connected via network 223, each component can be distributed over any suitable hardware system or collected into a single hardware system. For example, in some embodiments, production storage 261, production application server 231, production terminal 201 and analysis server 225 are all provided by an analytical unit of an NGS sequencing system, accessing a database according to embodiments of the invention and assembling sequence reads from NGS and reporting results through the terminal hardware (e.g., monitor, keyboard, and mouse) connected directly to the NGS system. In some embodiments, this functionality is provided as a "plug in" or functional component of sequence assembly and reporting software such as, for example, the GS De Novo Assembler, known as gsAssembler or Newbler (NEW assemBLER) from 454 Life Sciences, a Roche Company (Branford, Conn.). Newbler is designed to assemble reads from sequencing systems such as the GS FLX+ from 454 Life Sciences (described, e.g., in Kumar, S. et al., Genomics 11:571 (2010) and Margulies, et al., Nature 437:376-380 (2005)). In some embodiments, a production application is provided as functionality within a sequence analyzing system such as the HiSeq 2500/1500 system or the Genome AnalyzerIiX system sold by Illumina, Inc. (San Diego, Calif.) (for example, as downloadable content, an upgrade, or a software component).

In certain embodiments, as shown, for example, in FIG. 10, using existing network technologies, components of the invention can be implemented in systems that include multiple hardware and software components, including both special purpose computing devices and general purpose computers running software applications of the invention. Components of systems of the invention can be distributed geographically. For example, assay pipelines can include laboratory facilities in separate geographical locations from the production or development terminals. Any application server or storage can be housed in server computer hardware as provided, for example, by server farms or cloud computing systems. Exemplary hardware for implementing systems and methods of the invention is discussed below.

Figure 11:
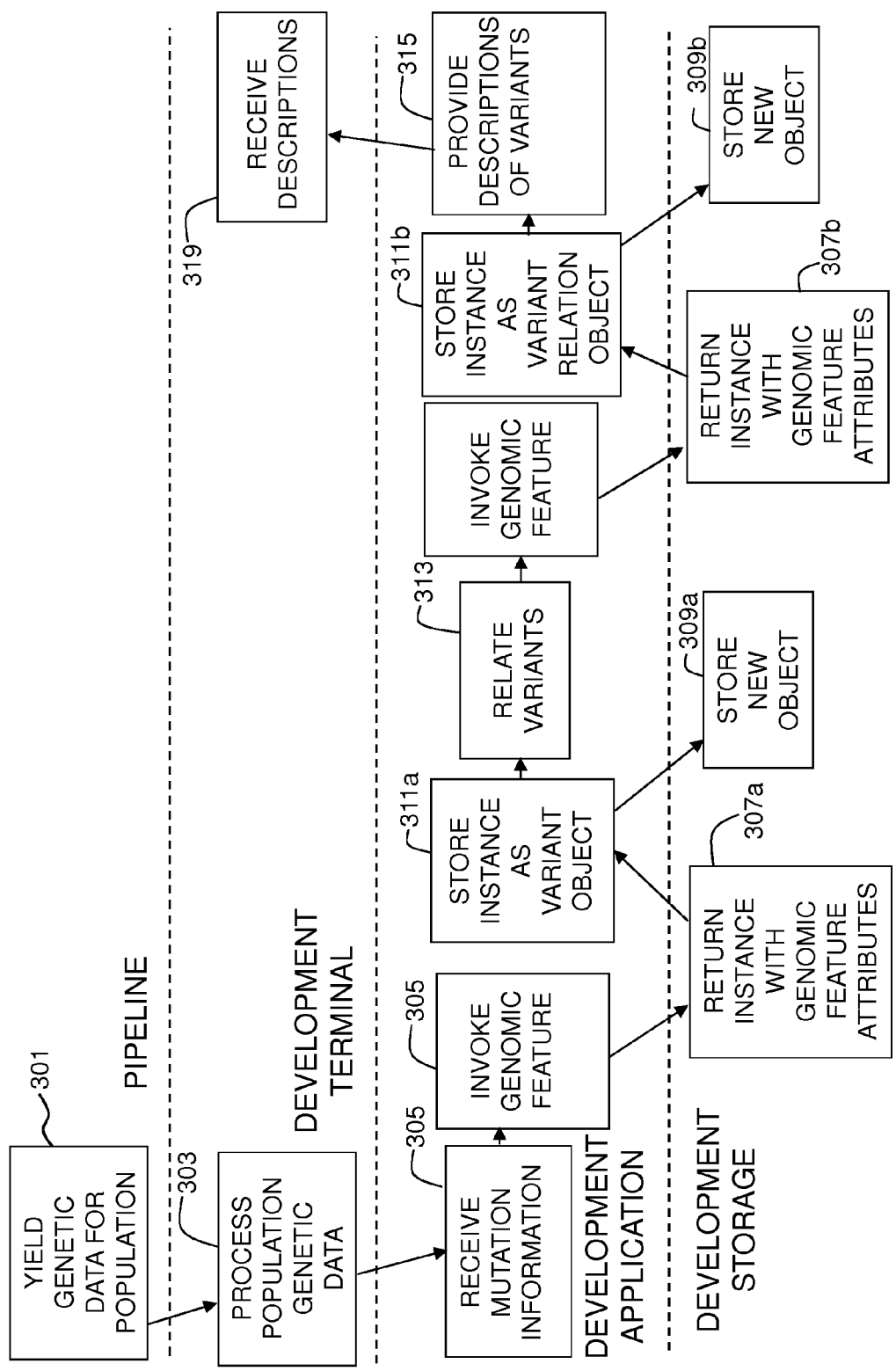
FIG. 11 diagrams development of a database of variant descriptions.

FIG. 11 shows development of a database of variants. Any assay pipeline, including laboratory work and literature reviews, can yield 301 raw genetic data relating to a relevant population, which is processed 303 via a development terminal. A development application operates, for example, on development application server 251 to receive 305 information identifying mutations based on the processed data. The development application invokes 306 the abstract class of genomic feature causing an instance of the object to be returned 307a from memory (e.g., memory 257 or storage 269) so that application 305 can store 311a a first variant as a variant object. In the development context, this object is stored 309a as a new object in the development database (e.g., and will be present in the production release). The creation of variant objects is optionally repeated until all received mutation information is represented. Processor 255 can then be used to relate 313 the variants and invoke the abstract class of genomic feature to return 307b an instance that is then stored 311b as a variant relation object. In the development context, this object is stored 309b as a new object in the development database (e.g., and will be present in the production release). With these objects created, the development application can then provide 315 descriptions of variants based, for example, on at least one of the variant relation objects. Development terminal 217 can be used to receive 319 any of these objects or descriptions, for example, to be curated by a geneticist to verify inclusion in the database, for QA/QC, or for production (e.g., in an integrated development/production environment).

With the development database thus created and populated, it can be released into production (i.e., step 3 in FIG. 9) for use in a clinical environment to produce reports including patient genotype information. In some embodiments, releasing to production includes anonymizing and abstracting the data. In fact, in some embodiments, strict separation is maintained among the development and production systems.

Figure 12:
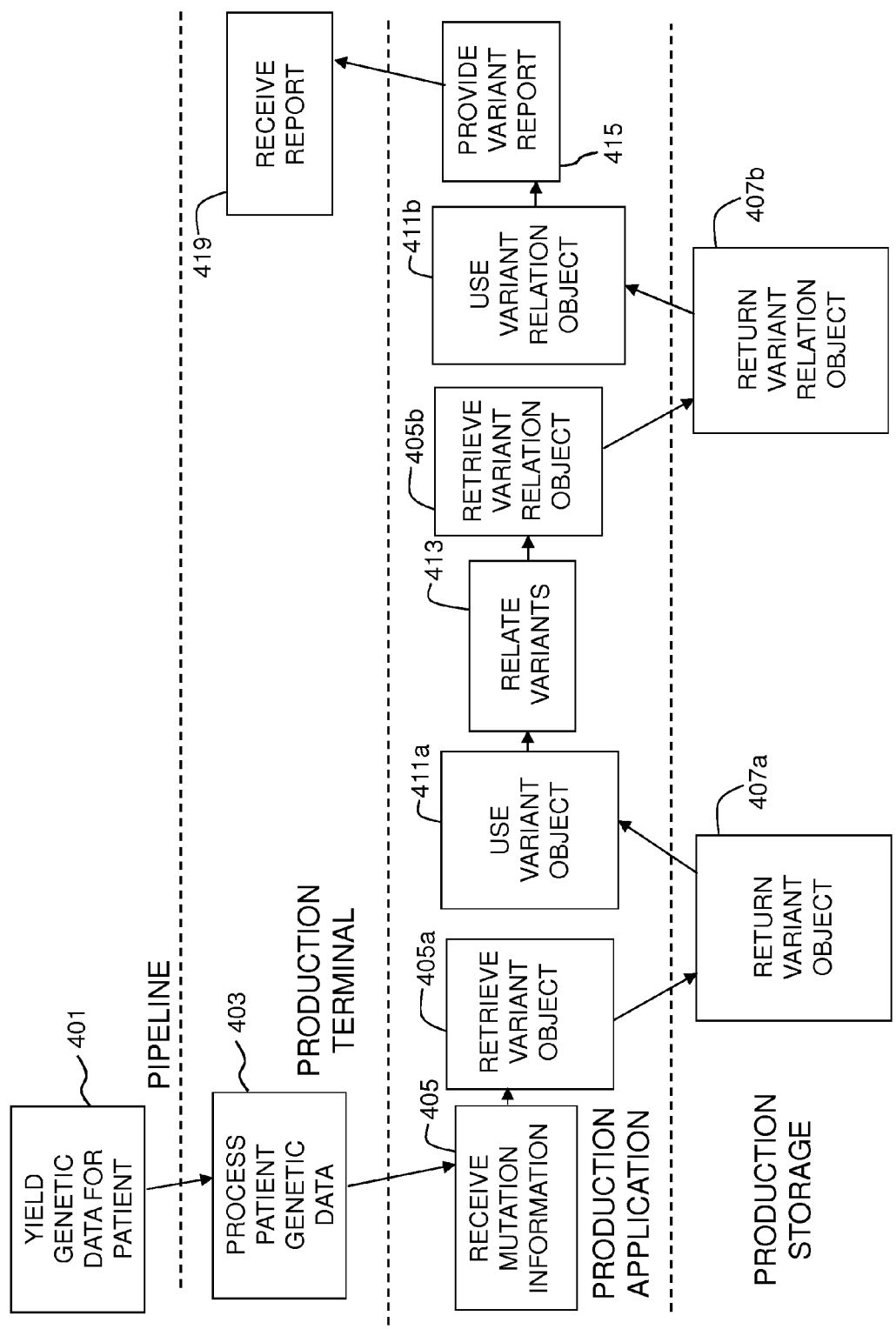
FIG. 12 diagrams systems and methods for providing a variant report an individual.

FIG. 12 shows use of the invention to provide a description of variants for an individual. As shown by FIG. 12, one or more assay pipelines such as any of those discussed herein are used to yield 401 genetic data for a patient, which can then be processed 403 at production terminal 201 (e.g., manually or automatically). A production application on production application server 231 receives 405 information from the assay pipeline results that identifies mutations, or variants, in the patient. The production application is then used to retrieve 405a the genomic feature object causing it to be returned 407a from the production database (e.g., in production storage 261). The production application can thus use 411a this object in local memory and repeat, as needed, to obtain a variant object for each mutation represented in the genetic data. Processor 235 can be used to relate 413 the objects by determining a relationship between mutations. Each relationship can be reported by retrieving 405b the appropriate object in the database, causing the object to be returned 407b from the production database (e.g., in production storage 261) thereby using 411b it in report production. The production application can then use the relation object to provide 415 a description of genetic variants for the patient, which in certain embodiments is received 419 at production terminal 201 for review by a physician or incorporation into a patient report.

While described generally in terms of on-line transaction processing (OLTP), it will be appreciated that embodiments of the invention further may be employed in on-line analytical processing (OLAP) and decision support systems (DSS). For example, in some embodiments, research application server 241 and research storage 265 provide a DSS/OLAP system.

FIG. 13 provides characteristics of OLTP and OLAP embodiments of the invention. In general as described herein, systems and methods of the invention include an application-oriented database for day-to-day operation in a clinical enterprise. Hardware and software is configured and optimized to support a high throughput of short transactions. However, in some embodiments, systems and methods of the invention provide a subject-oriented database to support complex queries comprising many scans to summarize and consolidate historical data to provide multidimensional analytical tools. Thus, in some embodiments, the invention supports data mining, and methods can layer predictive/statistical methods to inform likelihood of discovered relationships and possible causality.

By providing descriptions of variants in an agile, OLTP framework based on an object-oriented relational database schema, systems and methods of the invention can reliably and rapidly produce patient reports as assay pipeline results are obtained. Patient reports can include information about known and novel mutations, including mutations known to be, or suspected to be, disease associated. In certain embodiments, systems and methods of the invention are used to produce patient reports based on variants and relations among them in a patient's genome and to provide diagnostic, prognostic, or treatment information about associated medical conditions. Database records and patient reports can contain information relating to a variety of conditions including, for example, cancer, cystic fibrosis, Tay-Sachs disease, Canavan disease, fragile X, familial dysautonomia, Bloom syndrome, Fanconi anemia group C, Gaucher disease, mucolipidosis type IV, Niemann-Pick disease type A, spinal muscular atrophy (SMA), Sickle cell anemia, Thalassemia, or novel mutations.

Other embodiments are within the scope and spirit of the invention. For example, due to the nature of software, functions described above can be implemented using software, hardware, firmware, hardwiring, or combinations of any of these. Features implementing functions can also be physically located at various positions, including being distributed such that portions of functions are implemented at different physical locations.

As one skilled in the art would recognize as necessary or best-suited for performance of the methods of the invention, systems of the invention include one or more processors (e.g., a central processing unit (CPU), a graphics processing unit (GPU), etc.), computer-readable storage devices (e.g., main memory, static memory, etc.), or combinations thereof which communicate with each other via a bus.

In an exemplary embodiment shown in FIG. 10, a system can include assay pipelines 211 that provide genetic information directly into development and production or assay pipelines 215 that include analysis computer 215 (including, e.g., one or more of processor 227 and memory 229) to analyze results and provide those results.

Steps of the invention may be performed using development application server 251, production application server 231, research application server 241, or a combination thereof. Each server may be engaged over network 223, or directly, to each other or one of terminal 201 or 217. Preferably, production data is segregated from research data or development data. In fact, one benefit of systems structured according to embodiments disclosed herein is that the inherent structural segregation of research, development, and production components of the system facilitate segregation of the data. This allows, for example, the production application to operate without raising regulatory complexities that may be associated with some patient data.

Systems of the invention may include one or more computers. For example, any of the terminals, servers, and storage devices depicted in FIG. 10 can be, or can be implemented with, one or more computers. A computer generally includes one or more processors, computer-readable storage devices, and input/output devices.

A processor may be any suitable processor such as the microprocessor sold under the trademark XEON E7 by Intel (Santa Clara, Calif.) or the microprocessor sold under the trademark OPTERON 6200 by AMD (Sunnyvale, Calif.).

A computer-readable storage device (e.g., memory 207, 221, 237, 247, 257, or 229 or any of storage 261, 265, or 269 in FIG. 10) according to the invention can include any machine-readable medium or media on or in which is stored instructions (one or more software applications), data, or both. The instructions, when executed, can implement any or all of the functionality described herein. The data can be the genomic data as described herein. The term "computer-readable storage device" shall be taken to include, without limit, one or more disk drives, tape drives, memory devices (such as RAM, ROM, EPROM, etc.), optical storage devices, and/or any other non-transitory and tangible storage medium or media.

Input/output devices according to the invention may include a video display unit (e.g., a liquid crystal display (LCD) or a cathode ray tube (CRT) monitor), an alphanumeric input device (e.g., a keyboard), a cursor control device (e.g., a mouse or trackpad), a disk drive unit, a signal generation device (e.g., a speaker), a touchscreen, an accelerometer, a microphone, a cellular radio frequency antenna, and a network interface device, which can be, for example, a network interface card (NIC), Wi-Fi card, or cellular modem.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

The invention claimed is:

1. A method of describing mutations in a patient genome, the method comprising using a computer system comprising a memory coupled to a processor for:
   receiving data representing a first mutation and a second mutation in the patient genome;
   creating a first instance of an abstract class of genomic feature and storing in the first instance a number representing a start position in a reference human genome and at least one IUPAC character representing a nucleotide found in the patient genome at the start position and not found in the reference human genome;
   creating a second instance of the abstract class and storing in the second instance a second number representing a second start position, different from the first start position, in the reference human genome and at least one second IUPAC character representing a nucleotide found in the patient genome at the second start position and not found in the reference human genome;
   creating a third instance of the abstract class and storing in the third instance; the first instance, the second instance, and a description of a relationship between the first instance and the second instance; and
   describing the mutations in the patient genome based on the third instance.

2. The method of claim 1, further comprising:
   receiving data identifying a genomic region; and
   creating a fourth instance of the abstract class, the fourth instance comprising a description of a relationship between the genomic region and the first mutation and the second mutation.

3. The method of claim 2, wherein the genomic region is identified as one selected from the list consisting of: exon, intron, gene, and ORF.

4. The method of claim 2, wherein the genomic region is identified as one selected from the list consisting of: regulatory region, promoter, splice site, and non-coding region.

5. The method of claim 2, wherein the genomic region is identified as one selected from the list consisting of: epigenetically modified region and methylated sequence.

6. The method of claim 2, wherein the genomic region is identified as one selected from the list consisting of: protein motif and protein secondary structure.

7. The method of claim 1, wherein the first mutation is not already stored within the computer system.

8. The method of claim 7, further comprising storing the first instance in one or more computer storage devices.

9. A system for providing a description of a variant in a patient's genome, the system comprising:
   a processor; and
   a computer-readable storage device containing instructions which when executed by the processor cause the system to
   receive data representing a first mutation and a second mutation in the patient's genome;
   create a first instance of an abstract class of genomic feature and store in the first instance a number representing a start position in a reference human genome and at least one IUPAC character representing a nucleotide found in the patient genome at the start position and not found in the reference human genome;
   create a second instance of the abstract class and store in the second instance a second number representing a second start position—different from the first start position—in the reference human genome and at least one second IUPAC character representing a nucleotide found in the patient genome at the second start position and not found in the reference human genome comprising a description of the second mutation as a variant of the reference;
   create a third instance of the abstract class and store in the third instance; the first instance, the second instance, and a description of a relationship between the first instance and the second instance; and
   provide a description of the genome based on the third instance.

10. The system of claim 9, further operable to:
    receive data identifying a genomic region; and
    create a fourth instance of the abstract class, the fourth instance comprising a description of a relationship between the genomic region and the first mutation and the second mutation.

11. The system of claim 10, wherein the genomic region is identified as one selected from the list consisting of: exon, intron, gene, and ORF.

12. The system of claim 10, wherein the genomic region is identified as one selected from the list consisting of: regulatory region, promoter, splice site, and non-coding region.

13. The system of claim 10, wherein the genomic region is identified as one selected from the list consisting of: epigenetically modified region and methylated sequence.

14. The system of claim 10, wherein the genomic region is identified as one selected from the list consisting of: protein motif and protein secondary structure.

15. The system of claim 9, wherein the first mutation is not already stored within the system.

16. The system of claim 15, further operable to store the first instance in one or more computer storage devices.

* * * * *